(12) United States Patent
Robar

(10) Patent No.: US 11,911,632 B2
(45) Date of Patent: *Feb. 27, 2024

(54) SYSTEMS AND METHODS FOR MONITORING PATIENT MOTION VIA CAPACITIVE POSITION SENSING

(71) Applicant: DALHOUSIE UNIVERSITY, Halifax (CA)

(72) Inventor: James Leonard Robar, Halifax (CA)

(73) Assignee: Dalhousie University, Halifax (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,304

(22) Filed: Feb. 15, 2023

(65) Prior Publication Data

US 2023/0226376 A1  Jul. 20, 2023

Related U.S. Application Data

(63) Continuation of application No. 17/092,129, filed on Nov. 6, 2020, now Pat. No. 11,612,763, which is a (Continued)

(51) Int. Cl.
*A61N 5/10* (2006.01)
*A61B 5/11* (2006.01)
(Continued)

(52) U.S. Cl.
CPC .............. *A61N 5/1049* (2013.01); *A61B 5/05* (2013.01); *A61B 5/053* (2013.01); *A61B 5/1126* (2013.01);
(Continued)

(58) Field of Classification Search
CPC .... A61N 5/1037; A61N 5/1049; A61B 34/20; A61B 5/11; A61B 2034/2046; A61B 2034/2051; A61H 2201/5064
See application file for complete search history.

(56) References Cited

U.S. PATENT DOCUMENTS 5,279,309 A * 1/1994 Taylor .................... A61B 34/76
600/595
5,410,297 A 4/1995 Joseph et al.
(Continued)

FOREIGN PATENT DOCUMENTS

EP 2413091 A1 2/2012
GB 2094590 A 9/1982
(Continued)

OTHER PUBLICATIONS

Gladstone, D.J. et al., "Case report of a near medical event in stereotactic radiotherapy due to improper units of measure from a treatment planning system", Medical Physics Letter, vol. 38, No. 7, Jul. 2011.

*Primary Examiner* — Steven L Yeninas
(74) *Attorney, Agent, or Firm* — Todd A. Rattray, Oyen Wiggs Green & Mutala LLP

(57) ABSTRACT

Systems and methods are described for the monitoring of patient motion via the detection of changes in capacitance, as measured using a capacitance position sensing electrode array. The changes in capacitance may be processed to determine a corresponding positional offset, for example, using a calibration data set relating capacitance to offset for each electrode of the array. The detected positional offset may be employed to provide feedback to a surgeon or operator of a medical device, or directly to the medical device for the control thereof. A medical procedure may be interrupted when the positional offset is detected to exceed a threshold. Alternatively, the detected positional offset may be employed to manually or automatically reconfigure a medical device to compensate for the detected change in position. Various configurations of capacitive position sensing devices are disclosed, including embodiment in incor-
(Continued)

porating capacitive sensing electrodes with a mask or other support structure.

29 Claims, 14 Drawing Sheets

Related U.S. Application Data continuation of application No. 15/767,325, filed as application No. PCT/CA2016/051192 on Oct. 13, 2016, now Pat. No. 10,857,390.

(60) Provisional application No. 62/242,808, filed on Oct. 16, 2015.

(51) Int. Cl.
| | |
|---|---|
| *A61N 7/02* | (2006.01) |
| *A61B 90/18* | (2016.01) |
| *A61B 5/05* | (2021.01) |
| *A61B 34/20* | (2016.01) |
| *A61B 90/14* | (2016.01) |
| *G01V 3/08* | (2006.01) |
| *A61B 5/053* | (2021.01) |
| *A61B 5/00* | (2006.01) |
| *A61B 34/30* | (2016.01) |
| *A61N 5/06* | (2006.01) |
| *A61B 90/00* | (2016.01) |

(52) U.S. Cl.
CPC .............. *A61B 5/746* (2013.01); *A61B 34/20* (2016.02); *A61B 90/14* (2016.02); *A61B 90/18* (2016.02); *A61N 5/1039* (2013.01); *A61N 7/02* (2013.01); *G01V 3/08* (2013.01); *G01V 3/088* (2013.01); *A61B 34/30* (2016.02); *A61B 2034/2051* (2016.02); *A61B 2090/061* (2016.02); *A61B 2562/0214* (2013.01); *A61N 5/06* (2013.01); *A61N 5/10* (2013.01)

(56) References Cited

U.S. PATENT DOCUMENTS

| | | | |
|---|---|---|---|
| 5,463,388 | A | 10/1995 | Boie et al. |
| 5,628,315 | A | 5/1997 | Vilsmeier et al. |
| 5,651,044 | A | 7/1997 | Klotz, Jr. et al. |
| 5,702,406 | A | 12/1997 | Vilsmeier et al. |
| 5,805,664 | A | 9/1998 | Whipple, III et al. |
| 5,914,465 | A | 6/1999 | Allen et al. |
| 5,947,981 | A | 9/1999 | Cosman |
| 6,025,782 | A | 2/2000 | Newham |
| 6,246,900 | B1 * | 6/2001 | Cosman ................. A61B 34/20 606/130 |
| 6,288,707 | B1 | 9/2001 | Philipp |
| 6,297,738 | B1 | 10/2001 | Newham |
| 6,894,509 | B2 | 5/2005 | Johnson et al. |
| 7,570,064 | B2 | 8/2009 | Roziere |
| 8,330,474 | B2 | 12/2012 | Vandermeijden |
| 8,378,966 | B2 | 2/2013 | Oba et al. |
| 8,482,530 | B2 | 7/2013 | Bollinger |
| 8,653,835 | B2 | 2/2014 | Yamaguchi et al. |
| 9,492,107 | B2 | 11/2016 | Heismann |
| 2004/0017210 | A1 * | 1/2004 | Johnson ............... G01D 5/2417 324/661 |
| 2006/0030182 | A1 | 2/2006 | Gary, Jr. et al. |
| 2006/0093089 | A1 | 5/2006 | Vertatschitsch et al. |
| 2007/0205775 | A1 | 9/2007 | Voelkel et al. |
| 2008/0208063 | A1 | 8/2008 | Brauers et al. |
| 2009/0003523 | A1 * | 1/2009 | Raanes ................ A61N 5/1049 378/65 |
| 2009/0209852 | A1 | 8/2009 | Mate et al. |
| 2010/0127970 | A1 | 5/2010 | Oba et al. |
| 2012/0043475 | A1 | 2/2012 | Ahn |
| 2012/0323062 | A1 | 12/2012 | Wright et al. |
| 2013/0257784 | A1 | 10/2013 | Vandermeijden et al. |
| 2014/0193058 | A1 | 7/2014 | Bharat et al. |

FOREIGN PATENT DOCUMENTS

| | | |
|---|---|---|
| WO | 02053028 A2 | 7/2012 |
| WO | 2014025353 A1 | 2/2014 |
| WO | 2014045562 A1 | 3/2014 |
| WO | 2014182824 A2 | 11/2014 |
| WO | 2014205356 A2 | 12/2014 |
| WO | 2015141353 A1 | 9/2015 |

* cited by examiner

SYSTEMS AND METHODS FOR MONITORING PATIENT MOTION VIA CAPACITIVE POSITION SENSING

CROSS-REFERENCE TO RELATED APPLICATION

This application is a continuation of U.S. application Ser. No. 17/092,129 filed 6 Nov. 2020, which in turn is a continuation of U.S. application Ser. No. 15/767,325 having a filing date of 10 Apr. 2018, which in turn is a 371 of PCT Application No. PCT/CA2016/051192 filed 13 Oct. 2016, which claims priority to U.S. Application No. 62/242,808 entitled "SYSTEMS AND METHODS FOR MONITORING PATIENT MOTION VIA CAPACITIVE POSITION SENSING" and filed on 16 Oct. 2015. For purposes of the United States of America, this application claims the benefit under 35 U.S.C. § 119 of U.S. Application No. 62/242,808 filed 16 Oct. 2015, the entire contents of which is incorporated herein by reference.

External beam radiation therapy (RT) and stereotactic radiosurgery (SRS) require delivery of precisely defined x-ray beams to pre-defined locations within the human body in order to deliver a radiation dose sufficient to kill abnormal cells. While the most common indication of this treatment modality is cancer, radiation can also be used to treat an array of benign indications in the brain, including vestibular schwannoma, meningioma, pituitary adenoma, arteriovenous malformation, or functional disorders such as trigeminal neuralgia or Parkinson's disease. SRS involves the most demanding accuracy of delivery of radiation dose; for example, in treatment of trigeminal neuralgia, a very high dose, for example 90 Gy, is delivered in a single fraction to the trigeminal nerve, which is only millimeters in dimension. In these circumstances the motion of the patient during radiation delivery must be reduced to near zero. Current approaches to immobilizing the patient involve inserting pins into the skull, which are then secured to a stereotactic head frame—a practice that is invasive compared to other practices in radiotherapy.

For other cranial indications that are slightly less demanding with regard to spatial accuracy, in order to reduce the invasiveness of the treatment, a "frameless" approach can be used, for example, by reducing patient motion with a thermoplastic mask system or a bite-block. However, the motion during treatment (called intrafractional motion) with frameless systems can be significant compared to the required accuracy of radiation dose delivery. Furthermore, because for many treatment delivery systems there is no way to continuously monitor and adjust for this motion, spatial margins must be added to the treatment volumes during planning, which is equivalent to knowingly treating unnecessary regions of healthy brain. Moreover, since patient positioning usually degrades over the duration of treatment, this margin would be larger for longer treatment delivery times. For example, Kang et al. (Med Phys 40(5), 2013) measured 3D intrafractional motion for 262 patients using the Cyberknife system and concluded that margins of 2.1, 3.2 and 4.2 mm would be required for treatment sessions lasting 10, 20 and 30 minutes.

As noted above, therapeutic and surgical procedures, such as radiotherapy and radiosurgery, require positional monitoring when employed in a frameless configuration. Current methods of monitoring include imaging using ionization radiation (e.g. x-rays), real-time monitoring using radiofrequency (RF) transponders implanted into the patient, and optical monitoring of the patient's skin. Each of these methods have significant drawbacks, as explained below.

Imaging with x-rays adds inadvertent radiation dose to the patient. This is especially significant since many cranial indications are benign (e.g. acoustic neuroma, meningioma, pituitary functional disorders, trigeminal neuralgia) and patients are often young, which makes consideration of imaging dose and consequent radiation-induced carcinogenesis important, e.g., compared to treating high stage cancer. There are also technical restrictions, for example many x-ray systems are limited with regard to the temporal sampling of patient position and the source or detector may be blocked by the dose delivery platform (e.g. linear accelerator) during the treatment delivery.

Real-time monitoring using RF transponders involves implanting small metallic coils into the body, making the method invasive. The approach also involves a significant consumable cost, i.e., the transponders themselves, which has limited the adoption of the method in many countries where specific remuneration does not exist. In addition, the system is costly and involves purchase of an RF tracking panel and acquisition system that must be coupled to the treatment delivery platform.

Optical monitoring of the patient skin suffers from several drawbacks, including: i) possible skin deformation, causing skin to be a limited surrogate for tumor position, ii) limitation of the monitored area to one eight to one quarter of the upper facial skin, iii) detection of features in the optical signal that are not present in the reference data, e.g., hair, facial hair. These limitations are inherent to the method an unlikely to be resolved (Li et al, Med Phys 38(7), 2011).

As noted above, current commercial solutions involve potential harm to the patient (inadvertent use of x-rays), are invasive (RF transponders), or may give misleading information regarding actual tumor position (optical monitoring of skin).

SUMMARY

Systems and methods are described for the monitoring of patient motion via the detection of changes in capacitance, as measured using a capacitance position sensing electrode array. The changes in capacitance may be processed to determine a corresponding positional offset, for example, using a calibration data set relating capacitance to offset for each electrode of the array. The detected positional offset may be employed to provide feedback to a surgeon or operator of a medical device, or directly to the medical device for the control thereof. A medical procedure may be interrupted when the positional offset is detected to exceed a threshold. Alternatively, the detected positional offset may be employed to manually or automatically reconfigure a medical device to compensate for the detected change in position. Various configurations of capacitive position sensing devices are disclosed, including embodiments incorporating capacitive sensing electrodes with a mask or other support structure.

Accordingly, in a first aspect, there is provided a method of performing capacitive monitoring the position of a body region during a medical procedure involving a therapeutic or surgical device, the method comprising:

positioning the body region in a reference position associated with the medical procedure, wherein at least a portion of the body region is positioned within a sensing region of a capacitive position sensing device, the capacitive position sensing device comprising an array of electrodes, and wherein the body region is positioned without contacting the array of electrodes;

detecting capacitance between each electrode and the body region, thereby obtaining a set of measured capacitance values;

processing the set of measured capacitance values to determine a positional offset of the body region relative to the reference position; and controlling the therapeutic or surgical device based on the positional offset.

In another aspect, there is provided a method of performing capacitive monitoring of the orientation of a body region during a medical procedure involving a therapeutic or surgical device, the method comprising:

positioning the body region in a reference orientation associated with the medical procedure, wherein at least a portion of the body region is positioned within a sensing region of a capacitive position sensing device, the capacitive position sensing device comprising an array of electrodes, and wherein the body region is positioned without contacting the array of electrodes;

detecting a capacitance between each electrode and the body region, thereby obtaining a set of measured capacitance values;

processing the set of measured capacitance values to determine a angular offset of the body region about one or more axes relative to the reference orientation; and controlling the therapeutic or surgical device based on the angular offset.

In another aspect, there is provided a method of performing capacitive monitoring the position of a body region during a medical procedure, the method comprising:

positioning the body region in a reference position associated with the medical procedure, wherein at least a portion of the body region is positioned within a sensing region of a capacitive position sensing device, the capacitive position sensing device comprising an array of electrodes, and wherein the body region is positioned without contacting the array of electrodes;

detecting capacitance between each electrode and the body region, thereby obtaining a set of measured capacitance values;

processing the set of measured capacitance values to determine a positional offset of the body region relative to the reference position; and providing an alert to interrupt the medical procedure when the positional offset exceeds a threshold.

In another aspect, there is provided a system for performing capacitive monitoring the position of a body region during a medical procedure involving a therapeutic or surgical device, the system comprising:

a capacitive position sensing device comprising:
a dielectric support; and
an array of electrodes provided on or embedded within said dielectric support;

wherein said array of electrodes is configured for capacitive sensing within a sensing region, wherein the sensing region is suitable for positioning at least a portion of the body region therein, such that the body region is positionable in a reference position within the sensing volume without contacting said array of electrodes;

control and processing hardware operatively coupled to said capacitive position sensing device, wherein said control and processing hardware is connectable to said therapeutic or surgical device for sending a control signal thereto, and wherein said control and processing hardware is configured to perform operations comprising:

detecting capacitance between each electrode and the body region, thereby obtaining a set of measured capacitance values;

processing the set of measured capacitance values to determine a positional offset of the body region relative to the reference position; and providing the control signal to the therapeutic or surgical device based on the positional offset.

In another aspect, there is provided a system for performing capacitive monitoring the position of a body region during a medical procedure, the system comprising:

a capacitive position sensing device comprising:
a dielectric support; and
an array of electrodes provided on or embedded within said dielectric support;

wherein said array of electrodes is configured for capacitive sensing within a sensing region, wherein the sensing region is suitable for positioning at least a portion of the body region therein, such that the body region is positionable in a reference position within the sensing volume without contacting said array of electrodes;

control and processing hardware operatively coupled to said capacitive position sensing device, and wherein said control and processing hardware is configured to perform operations comprising:

detecting capacitance between each electrode and the body region, thereby obtaining a set of measured capacitance values;

processing the set of measured capacitance values to determine a positional offset of the body region relative to the reference position; and providing an alert to interrupt the medical procedure when the positional offset exceeds a threshold.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 1A shows an example implementation with a full ring, and FIG. 1B shows an alternative example implementation with a partial ring.

DETAILED DESCRIPTION

Figure 1A:
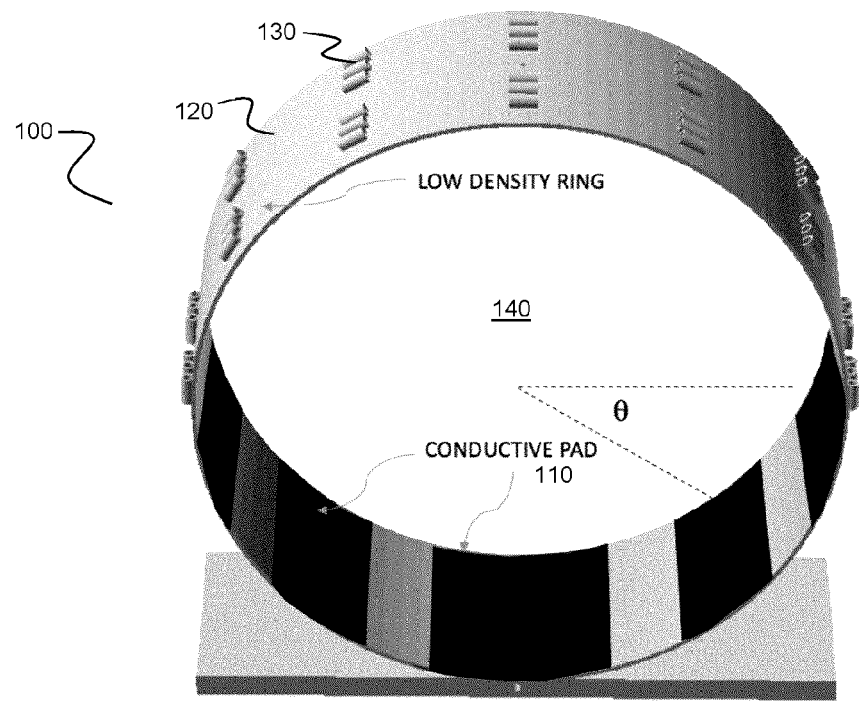
FIGS. 1A and 1B show an example capacitive position sensing device having a cylindrical ring geometry, where

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As used herein, the phrases "real-time" and "near-real-time" are intended to mean that positional offset detection is performed within a latency interval that is sufficiently low such that during the latency interval, the motion of the patient is sufficiently small to be clinically permissible. The latency interval may vary based on clinical application and context. In various embodiments, the latency interval may include a time range of, for example, microseconds, milliseconds, or seconds.

Unless defined otherwise, all technical and scientific terms used herein are intended to have the same meaning as commonly understood to one of ordinary skill in the art.

Capacitive Position Sensing for Monitoring Patient Motion

In view of the drawbacks of existing patient position monitoring methods described above, it is clear that a need exists for solution that provides accurate and non-invasive real-time monitoring of the patient position. Various example embodiments of the present disclosure address this need by providing a capacitive position sensing solution for the detection of the motion of a body region, such as the head. In some embodiments, capacitive position sensing is employed to detect and measure the positional offset of a body region in real-time or near-real-time, and the measured positional offset is employed to provide feedback to a medical procedure.

For example, in some example embodiments, an alert is provided, displayed, or otherwise communicated to a surgeon, operator, technician or other user when the detected positional offset exceeds a pre-selected threshold. In another example implementation, the alert is provided as a control signal that is employed to interrupt the operation of a medical device, such as a therapeutic or surgical device. In some example embodiments, the detected positional offset (e.g. caused by intrafractional motion) may be communicated to a surgeon, operator, technician or other user in order to allow the patient to be appropriately re-positioned. In another example embodiment, the detected positional offset may be provided to a medical device, such as a therapeutic or surgical device, so that the medical device can be reconfigured to compensate for the positional offset. Examples of therapeutic and surgical devices include, but are not limited to, radiotherapy devices, radiosurgical devices, and robotic therapy or surgical devices.

According to various embodiments, capacitive position sensing is performed via a capacitive position sensing device that includes an array of electrodes provided on or within a dielectric support, where each electrode is electrically addressable for the detection of capacitance. The array of electrodes are capable of sensing the capacitance within a sensing region adjacent to the electrode array, such that when at least a portion of a body region (i.e. a body part or anatomical part, such as the head) is placed within the sensing region, the capacitance between the electrode array and the portion of the body region is measurable when a suitable current or voltage is applied between respective electrodes of the electrode array and the body.

Unlike some of the aforementioned position monitoring devices known in the art, the devices, systems and methods of the present disclosure do not require direct contact with the patient (apart from optionally grounding the patient, as described below), thereby providing a non-invasive solution. Various embodiments disclosed herein also provide capacitance position detection without radiation in a passive configuration, apart from the application of electric fields, while remaining independent of the treatment delivery platform. Furthermore, as described below, various embodiments of the present disclosure are adaptable to common mask-type immobilization systems.

The position monitoring methods of the present disclosure may not be as sensitive to skin position or deformation as some of the known position monitoring devices described above. For example, in the case of the monitoring of the head of a patient, the capacitance methods disclosed herein may be sensitive to the patient bulk (e.g. entire cranium), as opposed to merely the skin (which can be a poor surrogate for the position of an internal organ or internal pathological structure, such as a tumor).

Furthermore, the systems and devices of the present disclosure may be beneficial in providing position monitoring at a lower cost that some of the aforementioned systems known to those skilled in the art.

Referring now to FIG. 1A, an example capacitance position sensing device 100 is shown, where the example capacitance position sensing device 100 includes a cylindrical dielectric support 120 having an array of capacitance sensing electrodes 110 distributed thereon. Each capacitance sensing electrode 110 (also referred to herein as a "conductive pad") is electrically addressable, for example, via electrical contacts 130 provided on the outer surface of dielectric support 120.

Figure 1B:
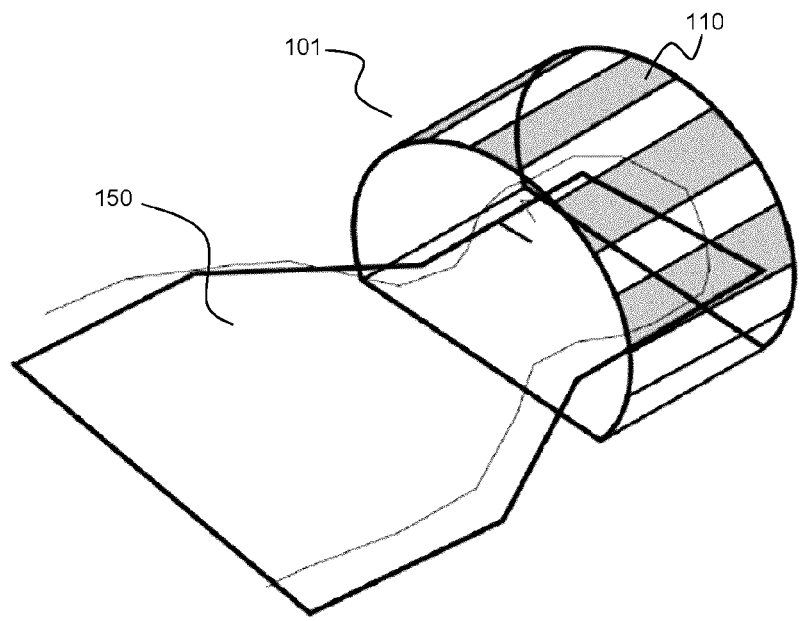

In the example electrode configuration shown in FIG. 1A, the capacitance sensing electrodes 110 are capable of sensing the capacitance associated with objects residing within sensing region 140. For example, the head of a patient, or a portion thereof, may be inserted within region 140 for capacitance-based position sensing. FIG. 1B illustrates an alternative example configuration involving a half-cylinder capacitance position sensing device 101, suitable for detecting positional offsets of a the head of a patient 150 based on capacitance detection via electrodes 110. The capacitance position sensing device could be employed to provide two or three-dimensional positioning information, depending on the orientation of the array electrodes.

It will be understood that electrical contact may be made with the electrodes 110 according to a wide range of methods, such as, for example, soldering or wire bonding, or via electrical connectors. The capacitance sensing electrodes are shown in FIG. 1A as being evenly distributed in an array, but it will be understood that the electrodes 110 need not be uniformly distributed, and that the configuration shown in FIG. 1A (and other figures of the present disclosure) are mere examples.

The suitable material composition and thickness of the capacitance sensing electrodes 110 and dielectric support 120 will vary depending on the clinical application, as described below.

Other Example Configurations of the Capacitance Position Sensing Device

It is noted that the capacitive position sensing device is not limited to a ring-type spatial configuration, and that a wide variety of electrode spatial configurations, and associated dielectric support structures, may be employed. For example, the dielectric support 120 need not have a circular shape, and can take on a wide variety of curved shapes (e.g. an oval shape), or a shape based on a plurality of flat segments (e.g. a rectangular shape), for example. In some embodiments, the spatial configuration of the array of electrodes may be determined based on that of an existing patient support structure, as described in further detail below.

Figure 2A:
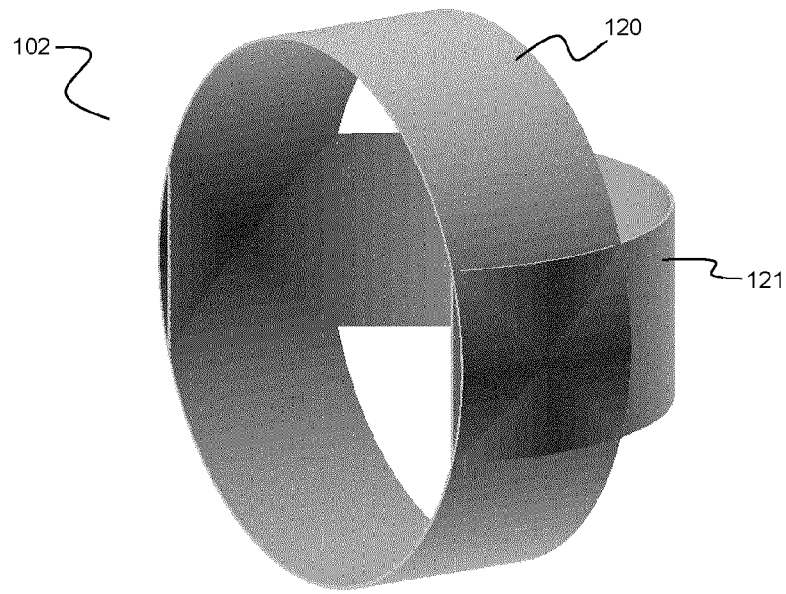
FIGS. 2A-C show several example alternative implementations of capacitive position sensing devices that employ multiple cylindrical portions.

Referring now to FIG. 2A, an alternative example embodiment is shown in which a second cylindrical segment 121, having a second array of capacitance sensing electrodes (not shown), is provided at an angle relative to the first dielectric support 120. Such an embodiment is capable of capacitance-based position sensing in three-dimensions, enabling, for example, the detection of positional offset in the z (i.e. cranial-caudal) dimension.

Figure 2B:
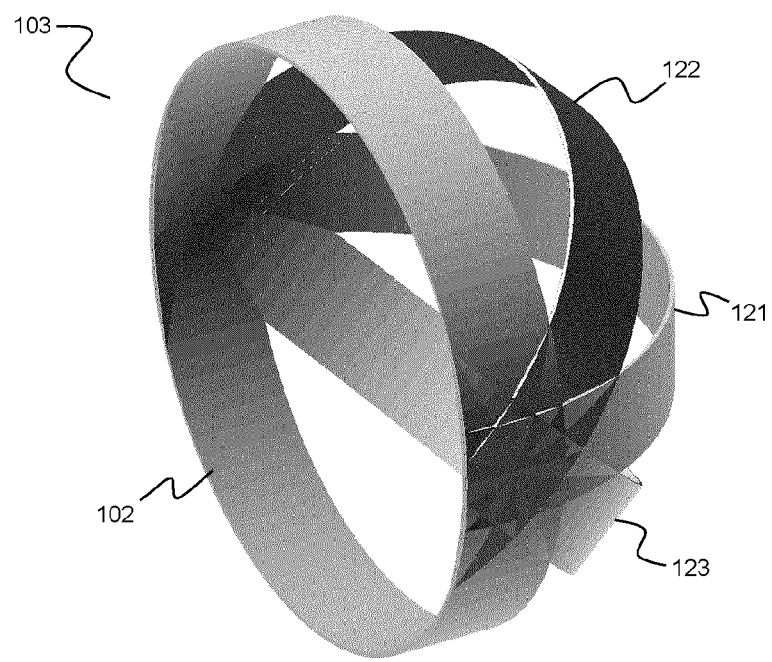
Figure 2C:
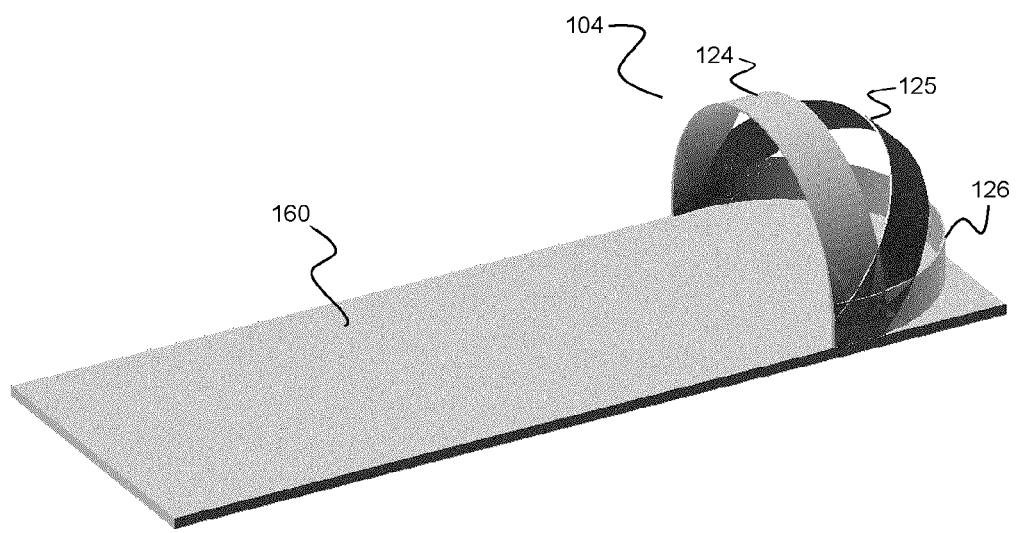

Although the first and second dielectric supports are shown in an orthogonal configuration, it will be understood that the relative angle between the two cylinder axes need not be 90 degrees, and that two or more additional cylindrical segments may be included. Examples of such an embodiment are shown in FIGS. 2B and 2C, where multiple half-cylindrical segments 121, 122 and 123 are shown in example capacitive position sensing device 103 of FIG. 2B, and multiple cylindrical segments 124, 125 and 126 are shown in the example capacitive position sensing device 104 of FIG. 2C. The example embodiment of FIG. 2C also shows the capacitive position sensing device 104 being supported by a patient support 160.

As noted above, the cylindrical embodiments shown in FIGS. 1A-B and FIGS. 2A-C are merely provided as illustrative embodiments, and a wide variety of electrode spatial configurations are envisioned without departing from the scope of the present disclosure. For example, in another example embodiment, the electrodes may be provided on a dielectric support having a spherical shape (i.e. the inner surface of the capacitive position sensing device is shaped as a portion of sphere). Moreover, although the preceding example embodiments illustrate capacitive position sensing devices that at least partially surround or house the body region, in other example embodiments, the capacitive position sensing device may be configured to be placed adjacent to the body region without surrounding the body region. It is expected that a suitable spatial configuration of the electrodes will vary depending on the type of medical procedure and the type of body region.

Calculation of Position from Capacitive Measurements

A conventional capacitor consists of two conductors, separated by a dielectric material. Each capacitance sensing electrode 110 (conductive pad) in the capacitance position sensing device acts as a single plate of a capacitor; when the body region of a patient or subject is introduced into, or adjacent to, or proximal to, the capacitance position sensing device, such that at least a portion of the body region lies within the sensing region, the intervening air acts as the dielectric and the patient acts as the second conductor. Since capacitance is defined as $$C=A\varepsilon/d$$

where A is the area of the conductor, $\varepsilon$ is the permittivity of the dielectric and d is the distance separating the conductors, variations in the distance between the patient and the electrodes of the capacitive position sensing device will produce corresponding variations in the measured capacitance in an inverse relationship.

Figure 3A:
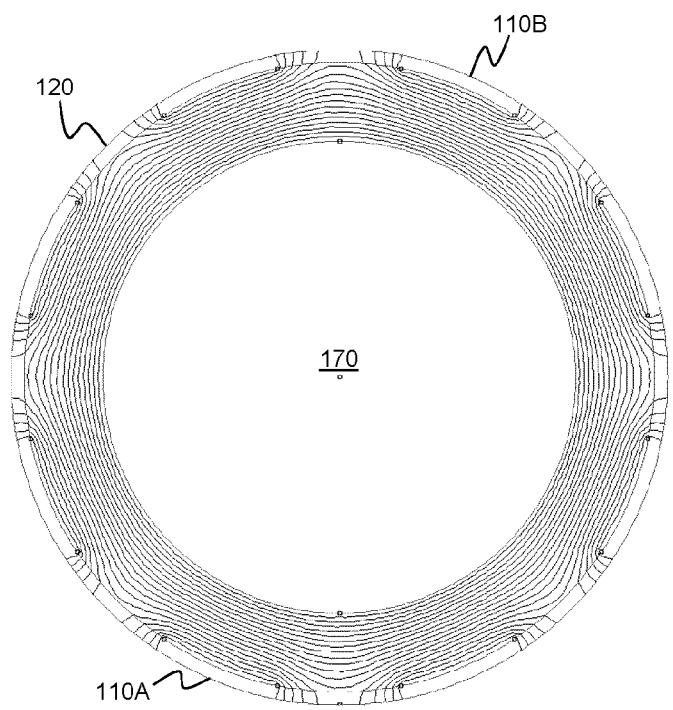
FIGS. 3A and 3B plot the results of simulations showing the equipotential lines between the array of electrodes of an example capacitive position sensing device and an cylindrical object placed within the sensing region of the device, showing the effect of a positional offset of the cylindrical object on the concentration of equipotential lines, demonstrating the varying capacitance that is spatially correlated with positional offset.
Figure 3B:
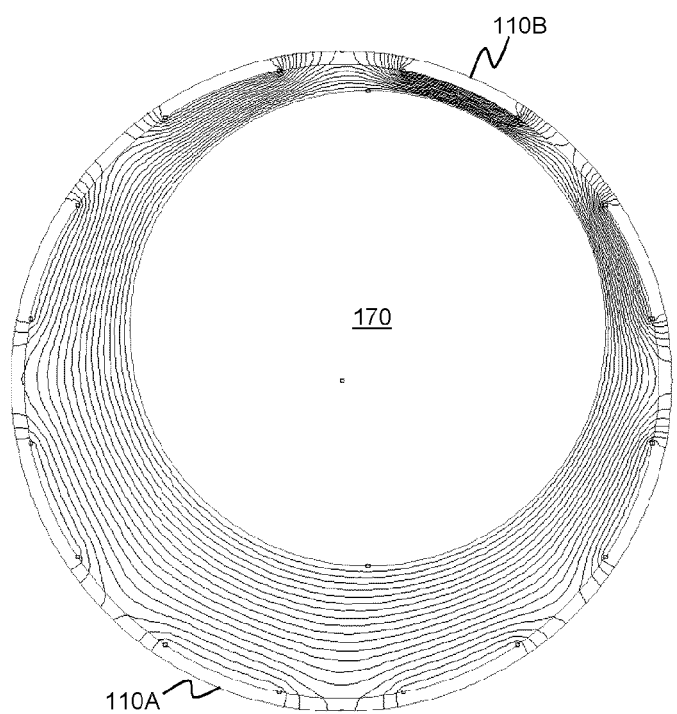
Figure 4A:
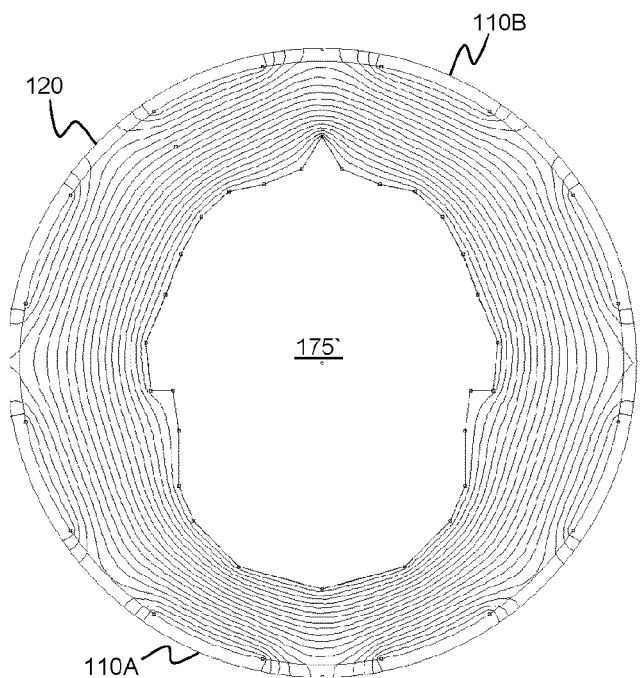
FIGS. 4A and 4B plot the results of simulations showing the equipotential lines between the array of electrodes of an example capacitive position sensing device and an head-shaped object placed within the sensing region of the device, showing the effect of a positional offset of the object on the concentration of the equipotential lines, demonstrating the varying capacitance that is spatially correlated with positional offset. The shape of the object was derived from computed tomography data of a patient.
Figure 4B:
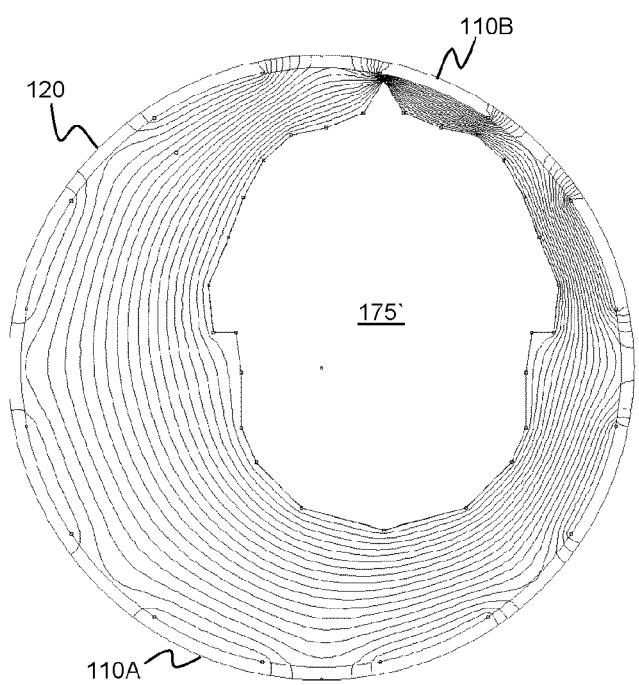

This position-dependence of the measured capacitance is illustrated in FIGS. 3A and 3B, which show the results of finite element analysis (FEA) simulations in the example case of a cylindrical body 170 positioned within the sensing region of a cylindrical capacitive position sensing device (such as the example embodiment shown in FIG. 1A). In FIG. 3A, the equipotential lines surround the grounded cylinder 170 and are symmetrically distributed with respect to the electrode array, such that the measured capacitance between each electrode and the cylinder is the same. For example, the density of equipotential lines between electrode 110A and the cylinder 170 is the same as the density of equipotential lines between electrode 110B and cylinder 170. FIG. 3B shows the changes in the equipotential lines that are caused by a positional offset of the cylindrical body 170. The positional offset has removed the symmetry, such that the density of equipotential lines now differs among the electrodes. For example, the density of equipotential lines is much higher between electrode 110B and the cylinder 170 than between electrode 110A and the cylinder 170. The positional offset is therefore encoded into the spatially-dependent capacitance values. FIGS. 4A and 4B show similar results for a body in the shape of a human head, where the shape was obtained from computed tomography of a subject.

The capacitance can be measured according to a wide range of capacitance detection methods known to those skilled in the art. Example methods of capacitance detection include, but are not limited to: applying a known charge to a pad and measuring potential; applying a known potential to a pad and measuring charge; constructing an oscillating circuit whereby the frequency of that circuit depends on capacitance, and measuring frequency. In another example implementation, a capacitance bridge may be employed to measure an unknown capacitance value. In one example embodiment, the electrodes of the array can be interrogated simultaneously for the detection of capacitance. In another example embodiment, the electrodes of the array can be interrogated sequentially for the detection of capacitance. For example, in the latter case, when a given electrode is not being interrogated, it could be grounded. Various capacitance detection devices are presently commercially available, such as the Freescale Semiconductor model MPR03X Proximity Capacitive Touch Sensor Controller.

In the examples described below, each conductive pad in the ring was connected to a capacitance sensor (e.g., MPR121, Freescale Semiconductor, Inc.), providing a set of capacitance measurements over the surface of the ring. By combining the measurements mathematically, the x and y position of the patient can be determined.

By combining and mathematically processing the set of capacitance values measured from the capacitive pads of the capacitive position sensing device, the positional offsets of the body region can be determined. Positional offsets indicate the spatial deviation of the patient from a reference position (baseline position). The baseline position can be determined, for example, through image guidance used routinely in the procedure, or via a positioning structure (e.g. a mask) against which the body region is initially positioned.

As described below, the positional offsets may be provided in multiple dimensions, such as two dimensions or three dimensions. For example, in two dimensions for the ring-type example embodiments shown in FIGS. 1A and 1B, $\Delta x$ and $\Delta y$ are the lateral and anterioposterior positional offsets, which may be determined using $$\Delta x = \sum_{i=1}^{n} k_i \cos\Theta_i$$

and $$\Delta y = \sum_{i=1}^{n} k_i \sin\Theta_i$$

where $C_i$ is the capacitance of the $i^{th}$ pad, and $\Theta_i$ is the angle between the horizontal axis and the centroid of the $i^{th}$ conductive pad. In the above equations, k is a capacitive pad-specific calibration function that may account for, for example, individual pad response, or the variation in sensitivity between pads for a given positional offset of the patient. For example, since distance between the capacitive plates varies as 1/C, this function may be expressed in the form $$k_i = R_i\left(M_i - \frac{1}{C_i}\right)$$

where $R_i$ and $M_i$ are constants determined empirically.

The sampling frequency of the detection of capacitance values may be selected to be sufficiently high in order to detect patient motion in real-time or near-real-time (e.g. intrafractional motion). It will be understood that a minimum sampling frequency may depend on a wide range of factors, including, but not limited to, the type of medical procedure, patient-specific aspects of the medical procedure (e.g. the size and geometry of a tumor), and the nature (e.g. amplitude and frequency range) of motion associated with a given patient. In some example embodiments, the sampling frequency of a given electrode may be selected to be greater than 10 Hz, greater than 100 Hz, greater that 1 kHz, greater than 10 kHz, or greater than 100 kHz. In some example embodiments, the frequency of positional offset detection, based on the interrogation of all electrodes and the processing of the set of capacitance values to infer positional offset, may be greater than 10 Hz, greater than 100 Hz, greater that 1 kHz, greater than 10 kHz, or greater than 100 kHz.

Calibration Methods

In some embodiments, calibration data is employed when processing the measured capacitance values to infer the spatial offset(s). In one example embodiment, the relationship between positional offset of the patient and capacitive measurements may be determined through an empirical calibration routine. For example, with the body region of the patient provided in a stationary configuration, the practitioner may apply known offsets to the capacitive position sensing device, for example, via manually or automated means. Such an embodiment avoids shifting the patient, and spatial offsets are equivalent to motion of the patient but opposite in direction. Alternatively, the body region may be translated by known amounts relative to the capacitive position sensing device.

For each known offset applied, all capacitive signals $C_i$ are read and related to the offset introduced. This may be repeated sequentially for the anterioposterior, lateral and superioinferior dimensions or combinations thereof. The result of this process is a set of (offset, capacitive reading) pairs. This calibration data set may be stored in several forms, for example, as a discrete data set that can be interpolated during subsequent processing, or parameterized, for example through curve fitting.

Figure 5C:
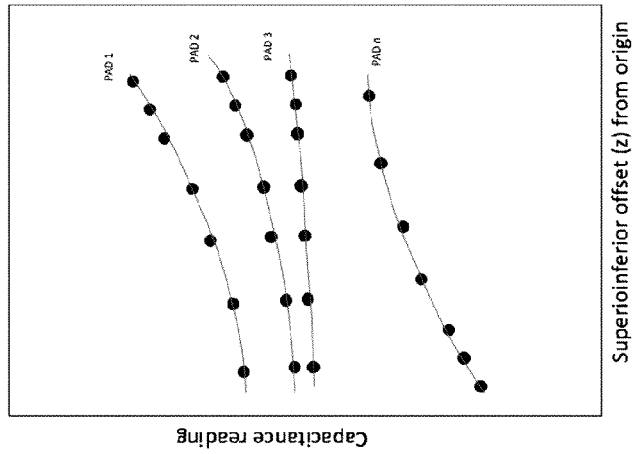
FIGS. 5A-C plot example calibration curves that relate known positional offsets to measured capacitance readings for an example cylindrical device. In this illustration, the measured object has been shifted relative to the capacitive array by seven offsets along each of the lateral, anteroposterior and superioinferior dimensions.
Figure 5B:
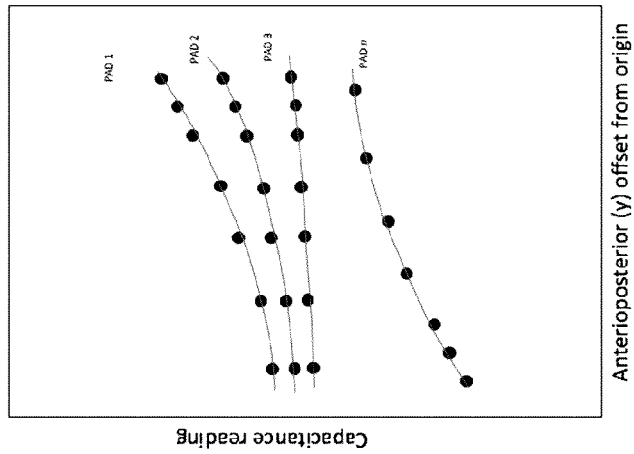
Figure 5A:
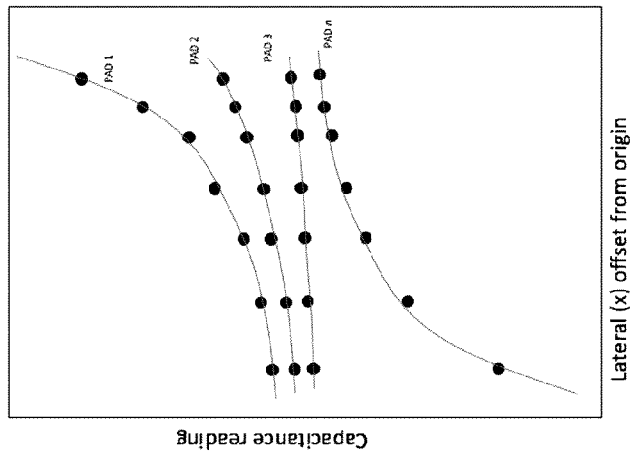
Figure 6A:
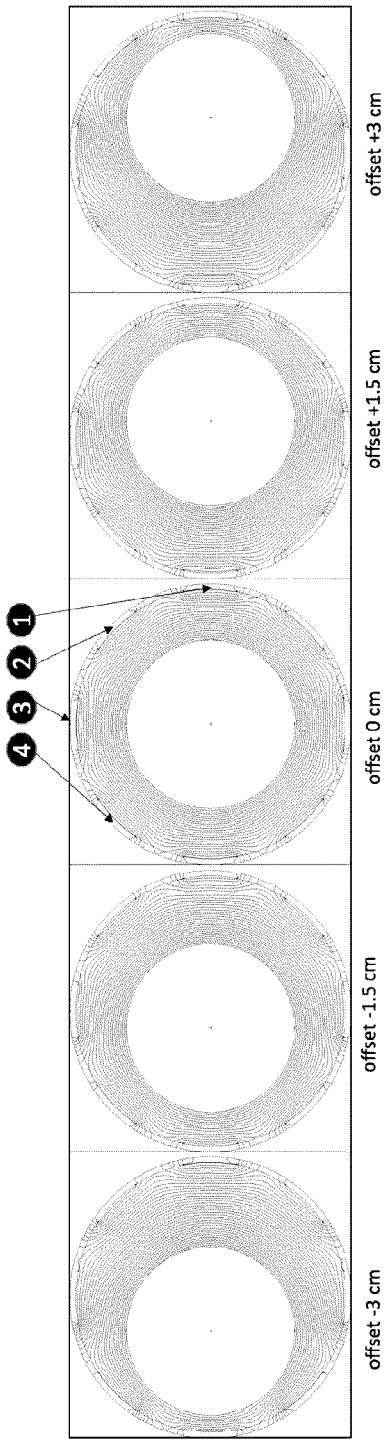
FIGS. 6A and 6B show (A) equipotential plots from a series of finite element models performed at different spatial offset values, and (B) positional offset calibration curves obtained based on the finite element model results for four example array electrodes.
Figure 6B:
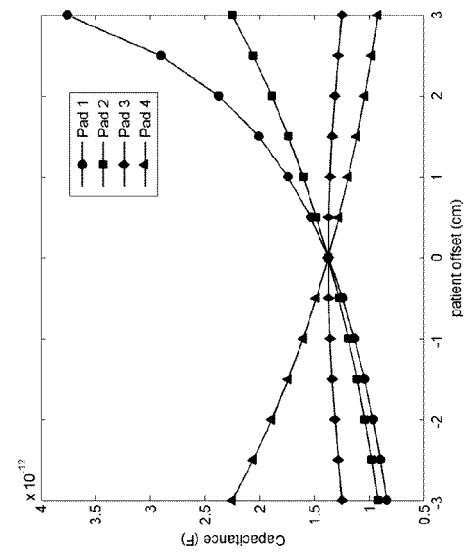

An example of parametric curve fitting of a subset of the calibration data set is shown in FIGS. 5A-C, where example calibration curves that relate known positional offsets to measured capacitance readings are plotted for an example cylindrical device. In this illustration, the measured object has been shifted relative to the capacitive array by seven offsets along each of the lateral, anterioposterior and superioinferior dimensions. For each offset, the capacitance reading for each of each capacitive pad is measured. For each pad, the relationship between capacitance and offset can be parameterized, for example, through curve fitting. FIGS. 6A and 6B show results from a second set of FEA simulations, in which the dependence of lateral offset of a cylindrical body is plotted for four selected electrodes, with each electrode exhibiting a unique dependence of capacitance on spatial offset.

The parameterization yields a series of expressions $$\Delta x_i = F_x(C_i)$$

$$\Delta y_i = F_y(C_i) \text{ and}$$

$$\Delta z_i = F_z(C_i)$$

where ($\Delta x$, $\Delta y$, $\Delta z$) are the three-dimensional positional offsets of the body region (e.g. cranium) and $F_x$, $F_y$ and $F_z$ are the relationships between positional offset to capacitance readings $C_i$ previously established.

Having obtained the calibration data set, the spatial coordinates of the body region may be determined based on a set of capacitance values, for example, by comparing the set of measured capacitance values to the calibration data set and selecting spatial offsets that produce the best match between the calibration data and the measured set of capacitance values.

In one example embodiment, one set of ($\Delta x$, $\Delta y$, $\Delta z$) coordinates may be separately calculated for each capacitance sensing electrode (capacitive pad). The algorithm calculating positional coordinates may report, for example, the mean spatial offset obtained from the set of capacitance sensing electrodes, and optionally one or more additional statistical measures, such as median and standard deviation. The per-electrode spatial offsets may also be compared in order to identify, and optionally discard, any spatial offsets that appear to be outliers (e.g. based on comparing the offset values for a given electrode to the average or standard deviation of the offset values for the remainder of electrodes). Alternatively, the algorithm may determine which pad is most sensitive to the offset which has occurred, given, for example, by the absolute offset of the capacitive reading from baseline or curvature of the parameterization for that measured capacitance value, and may calculate the positional offsets based on that capacitance reading alone. In yet another example embodiment, the determination of the spatial offset may be determined by applying weighting factors to the per-electrode spatial offset values when computing the net spatial offset, such that the spatial offset values corresponding to electrodes with the highest sensitivity (e.g. closed proximity) receive the highest weights.

This calibration procedure may be made practical and convenient for the clinical application. If the array is shifted by automated means, e.g., by actuators, this calibration may be performed in a time efficient manner. In addition, the calibration routine may be performed well in advance of the procedure and stored for later use, or performed in situ immediately prior to the procedure. Furthermore, an advantage of this empirical calibration approach is that it may be established on a per patient basis, such that the calibration data set is a per-patient calibration data set. Accordingly, if inter-patient variations exist with regard to the relationship between capacitance and positional offset, this may be accounted for during the calibration procedure.

In another example embodiment, the calibration data set may be generated, at least in part, via simulations involving a mathematical model. For example, FIG. 3A shows the result of a Finite Element Analysis (FEA) illustrating equipotential lines within a ring-geometry capacitive array, with a grounded cylinder 170 approximating the patient at the center of the ring. In the FEA, for any position of the patient within the capacitive array, the capacitance of each pad can be calculated, since both the charge and potential of the capacitive pads are returned by the analysis. If the simulated patient is then shifted as shown in FIG. 3B, new values of the capacitance of each pad can be calculated. By repeating this process over a range of positional offset values, patient position and capacitance values can be related and used in the generation of the calibration data set.

In some cases, the measured capacitance may depend significantly on the geometry of the patient, and a cylindrical approximation of the body region may not be sufficient. In such cases, a more realistic anatomical model may be employed. For example, an approximate model may be generated based on an atlas or based on a set of patients, or a per-patient model may be employed. For example, in radiotherapy or radiosurgery, it is standard practice to perform Computed Tomography (CT) imaging of the patient prior to the procedure for treatment planning purposes. In this application, CT image data may be used to generate a model within the FEA. An example of equipotential lines generated with a patient specific model is shown in FIG. 4A. As explained above, by introducing positional offsets of this simulated patient, as illustrated in FIG. 4B, a capacitance-to-position calibration may be realized. This approach is advantageous since it is patient-specific, may be conducted off-line well in advance of the patient's procedure, and uses the planning CT data which is available during the process of radiotherapy or radiosurgical treatment planning.

In another example embodiment, the spatial offset values may be determined without the need for a priori calibration data. Prior to initiating the medical procedure, the body region is positioned in the reference position. Capacitive sensing is then performed with the capacitive position sensing device, and the capacitive position sensing device is dynamically actuated, with a set of motors, in order to maintain, or best approximate, the initially measured set of capacitance values. The signals provided to the motors, and/or a measured positional change of the capacitance position sensing device, may be employed to infer the positional offset of the body region.

Other Design Variations

It will be understood that the number of electrodes in the array of electrodes of the capacitive position sensing device may vary from relatively few electrodes (e.g. our four conductive pads; left/right and anterior/posterior) to a much larger number of electrodes (e.g. 10, 20, 50, 100 or 200, or more). The number of electrodes needed may depend, for example, on the type of medical procedure, the size and geometry of the body region, and the desired response time of the device. An additional design consideration is the geometry of the electrodes, which can be solid or, for example, hatched.

Figure 7:
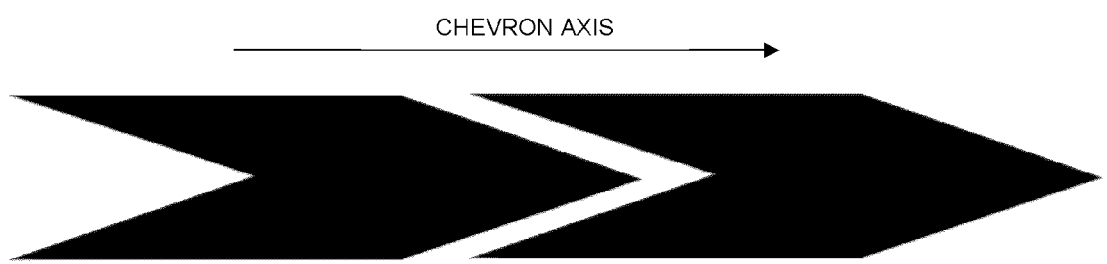
FIG. 7 illustrates an example electrode configuration in which two or more chevron-shaped electrodes are provided as electrodes in a capacitive position sensing device having a cylindrical configuration, such that the chevron axis is parallel to the cylinder axis.

In one example implementation involving a cylindrical geometry, electrodes could be arranged as a set of two or more adjacent chevrons that are spatially nested, where the axis of the chevrons is directed along the dimension that is perpendicular to the x-y plane of the cylinder array, as shown in FIG. 7. By comparing signal from the first and second chevron (or among more than two), information regarding z-position could be obtained. This could also be done with adjacent triangles, or other related geometrical shapes having vertices.

Additional optional design variations include the inclusion of electrical shielding and/or field focusing features. For example, shielding may be provided between pads or the entire array may be shielded.

Figure 8A:
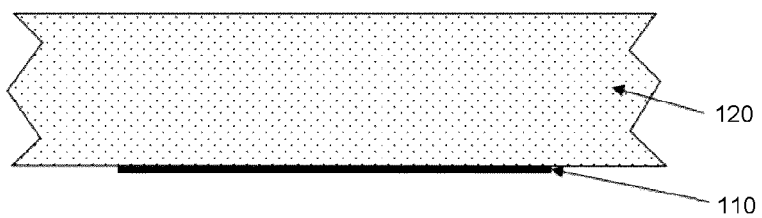
FIGS. 8A-D show example cross-sectional profiles of several possible configurations of the capacitive position sensing device.
Figure 8B:
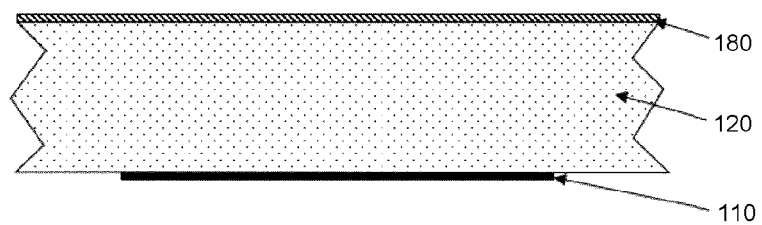
Figure 8C:
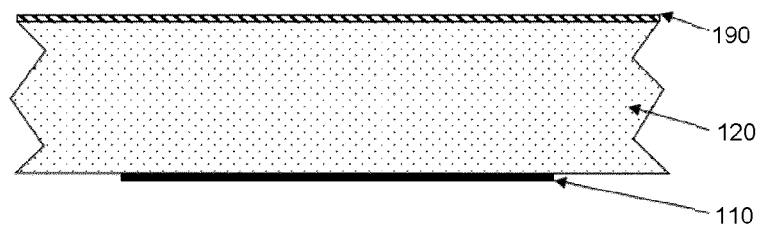
Figure 8D:
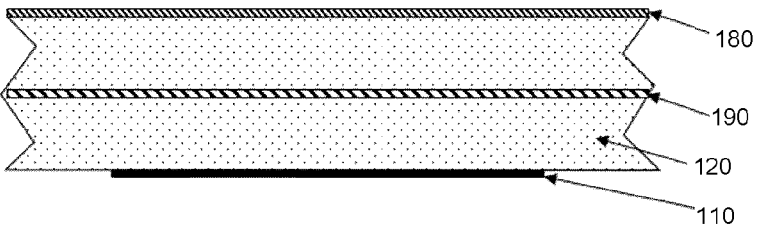

FIGS. 8A-D show possible cross-sections of the device, where FIG. 8A shows an example embodiment in which capacitive sensing electrode 110 is provided on the back of dielectric support 120. FIG. 8B shows an alternative example embodiment in which an electromagnetic shielding layer 180 is included on the top surface of the dielectric support 120, as it may be advantageous in some applications to add an electromagnetic shielding layer to minimize the effects of stray electromagnetic fields in the vicinity of the device. In addition, for some applications it may be beneficial to add a field-defining layer 190, as shown in FIG. 8C, in order to focus electric fields produced by charge on the capacitive pads to the inner region of the capacitive array. For example, an electric potential equal or close to that of the capacitive pads may be applied to the field-defining layer. As shown in FIG. 8D, the device may also be constructed to include both the electromagnetic shielding layer 180 and the field-defining layer 190. The layers of the device may be constructed of rigid or flexible materials, depending on the application. For example, the electrodes and dielectric backing may be provided as a flexible substrate, such as a flex circuit.

As noted below, in radiosurgical or radiotherapeutic applications in which the capacitive positioning sensing device is positioned such that the radiation beam passes through the device when irradiating the body region, the dielectric support 120, electrodes 110, and electromagnetic shielding layer 180 and field-defining layer 190 (when present), should introduce minimal attenuation of the radiation beam, such that a sufficient flux and/or intensity of the beam is delivered to the body region.

Figure 9:
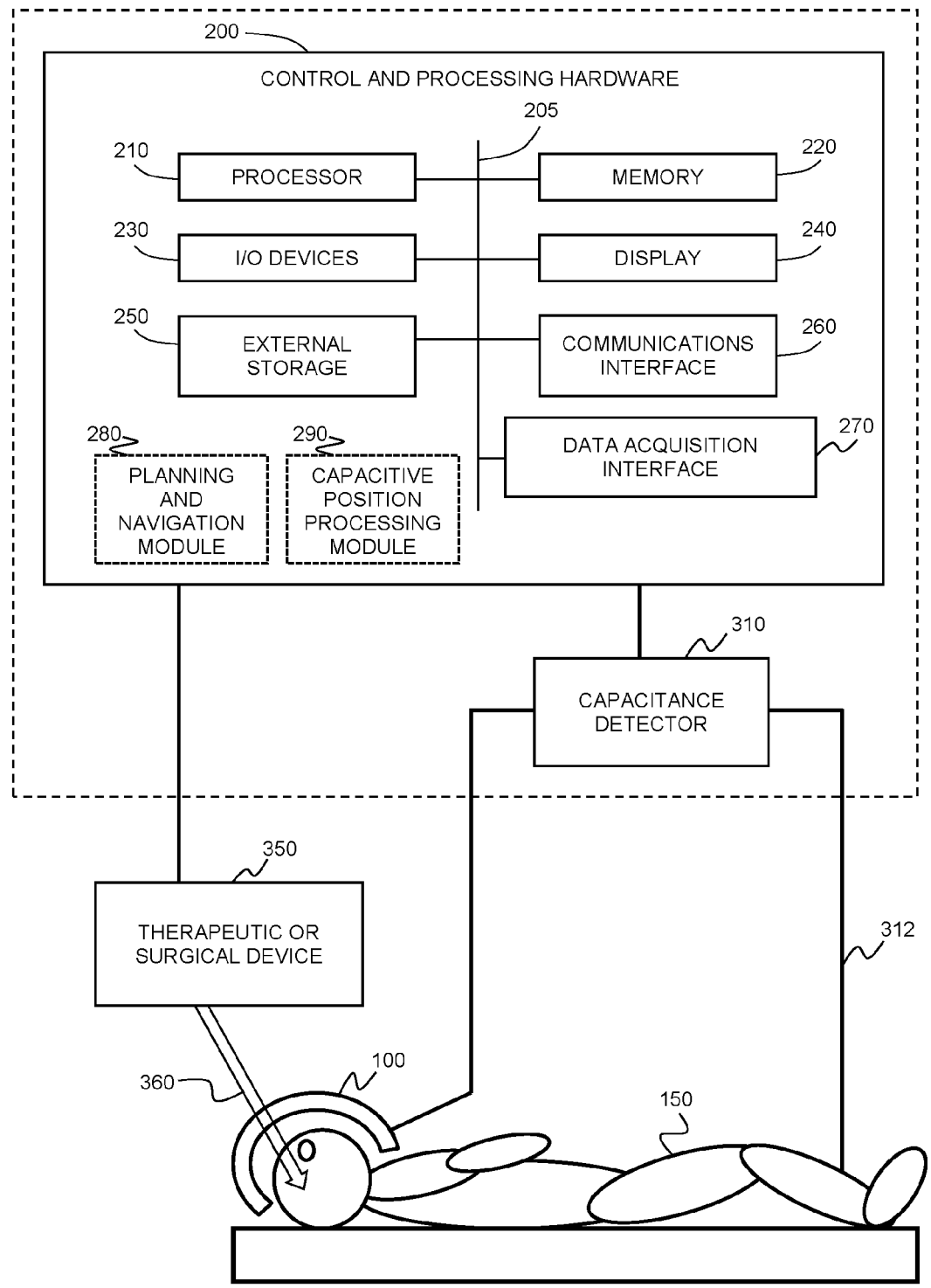
FIG. 9 is a diagram of an example system for performing capacitive position monitoring during a medical procedure.

Example System Configuration for Performing Capacitive Position Monitoring During a Medical Procedure Referring now to FIG. 9, an example system is shown for performing capacitive position monitoring during a medical procedure. The example system includes a capacitance position sensing device 100, placed in close proximity to the body region of the patient for monitoring the positional offset thereof (in the illustrated example, the body region is the head).

Capacitive position sensing device 100, which includes an array of capacitive sending electrodes as described above, is interfaced with capacitance detector 310, such that each electrode is separately addressable. The capacitance detector 310 is configured to detect the capacitance between each electrode of the array of electrodes of the capacitive positioning sensing device 100 and the body 150. Capacitance detector 310 may employ any suitable method of capacitance detection, including, but not limited to, any of the method described above. As shown in the figure, the capacitance detector 310 may provide a reference or ground connection (e.g. electrode) 312 that is brought into in electrical communication with the patient's body 150, directly or indirectly. Although, in some implementations, the patient's body may be grounded, it will be understood that grounding may not be required in order to measure capacitance.

Capacitance detector 310 is interfaced with control and processing hardware 200, which is receives sets of capacitance values from capacitance detector 310, and optionally controls capacitance detector such that set of capacitance values are measured at prescribed time intervals. As shown in the example embodiment illustrated in FIG. 9, control and processing hardware 200 may include a processor 210, a memory 220, a system bus 205, one or more input/output devices 230, and a plurality of optional additional devices such as communications interface 260, display 240, external storage 250, and data acquisition interface 270.

The present example methods of performing capacitive position sensing can be implemented via processor 210 and/or memory 220. As shown in FIG. 9, the positional offset is calculated by control and processing hardware 200, via executable instructions represented as capacitance position processing module 290. The control and processing hardware 200 may include and execute instructions for planning and navigation of a medical or surgical procedure, as shown by planning and navigation module 280.

As shown in FIG. 9, control and processing hardware 200 may be interfaced with a medical device, such as therapeutic or surgical device 350, for providing control signals thereto. In one example implementation, control and processing hardware 200 is programmed with a pre-selected offset threshold, such that when the positional offset exceeds the offset threshold, a control signal is provided to the therapeutic or surgical device 350 to interrupt its operation (e.g. turning off a radiation beam, or interrupting beam delivery via an interlock). In one example implementation, two or more thresholds may be provided, where each threshold corresponds to a different spatial direction or dimension. In another example implementation, the positional offsets are provided to the therapeutic or surgical device 350 such that the therapeutic or surgical device can compensate for changes in the position of the body region. In another example implementation, the positional offsets are provided to the therapeutic or surgical device or to a navigation or planning system associated with the device, such that the location of one or more target locations associated with the medical procedure are dynamically updated. In another example implementation, the positional offsets are employed to control the position and/or orientation of the therapeutic or surgical device to compensate for changes in the position of the body region.

Figure 10:
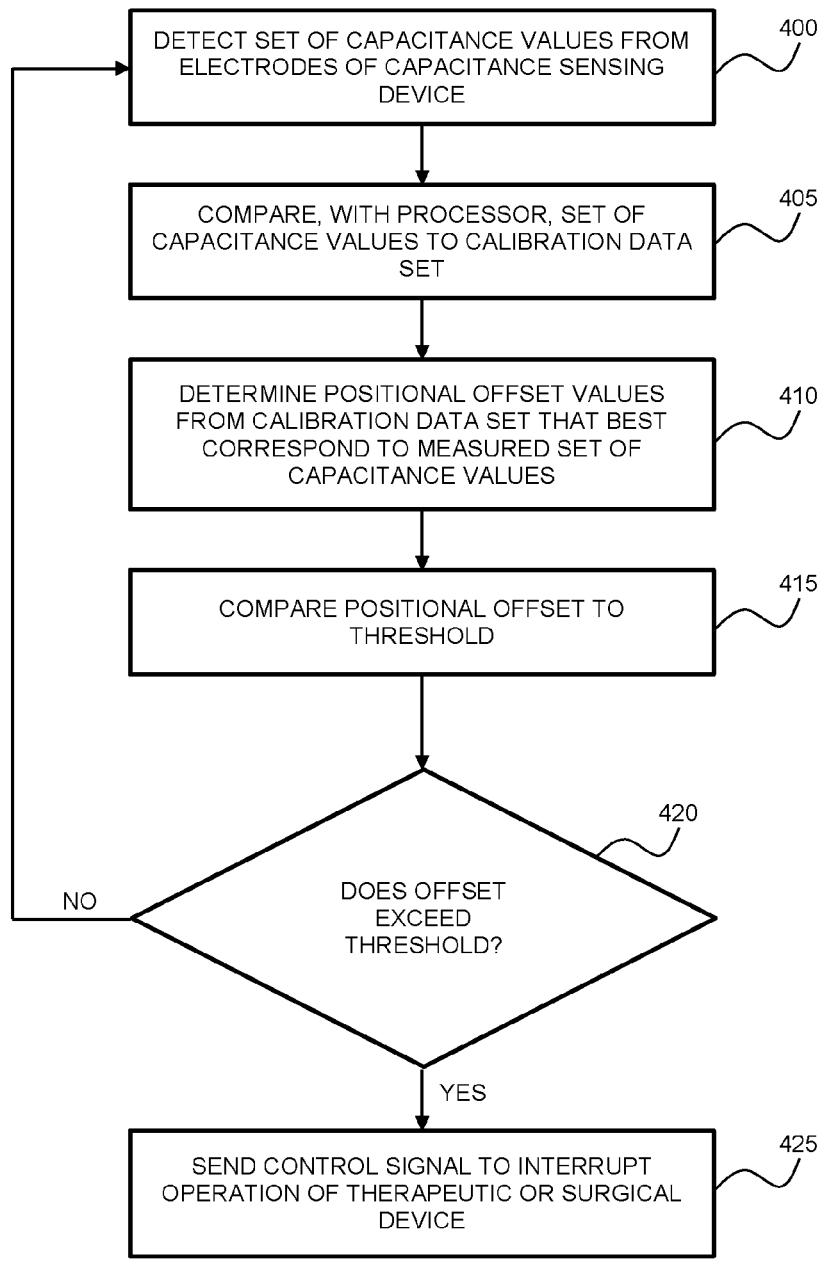
FIG. 10 is a flow chart illustrating an example method of controlling a therapeutic or surgical device based on capacitive position sensing.

FIG. 10 provides a flow chart illustrating an example method of controlling the operation of a therapeutic or surgical device in response to a positional offset detected with a capacitive position sensing device, where the operation of the device is interrupted when the measured offset exceeds a pre-selected threshold. In step 400, a set of capacitance values are detected from the electrodes of the capacitance sensing device. These capacitance values processed and compared, in step 405, to a calibration data set. Positional offset values are then obtained, in step 410, from the calibration data set, where the positional offset values best correspond to the measured set of capacitance values. The positional offset values are then compared to a threshold in step 415, and if the positional offset values offset exceed the threshold (see step 420), then a control signal is sent to interrupt operation of a therapeutic or surgical device, as in step 425.

In alternative embodiments, the control and processing hardware 200 provide feedback to an operator, surgeon, technician, or other user, such that the user can intervene and control the operation of the therapeutic or surgical device based on the detected positional offset. In one example implementation, the control and processing hardware 200 is programmed with a pre-selected offset threshold, such that when the positional offset exceeds the offset threshold, an alert is communicated (e.g. via an audible alarm and/or visual indication on a display device). In another example implementation, the detected positional offsets may be communicated to the user (e.g. via information displayed on a user interface), such that the therapeutic or surgical device, or a planning or navigation system associated with the device, can be reconfigured to compensate for changes in the position of the body region.

The functionalities described herein can be partially implemented via hardware logic in processor 210 and partially using the instructions stored in memory 220. Some embodiments may be implemented using processor 210 without additional instructions stored in memory 220. Some embodiments are implemented using the instructions stored in memory 220 for execution by one or microprocessors. Thus, the disclosure is not limited to a specific configuration of hardware and/or software.

It is to be understood that the example system shown in FIG. 9 is not intended to be limited to the components that may be employed in a given implementation. For example, the system may include one or more additional processors. Furthermore, one or more components of control and processing hardware 200 may be provided as an external component that is interfaced to a processing device. For example, as shown in the figure, capacitance detector 310 may be included as a component of control and processing hardware 200 (as shown within the dashed line), or may be provided as one or more external devices.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed herein can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

Potential Applications

In concept the device could be used in any application where a rapid (e.g. real-time or near real-time), non-contact, non-invasive readout of position of the head (e.g. cranium) or other body region (i.e. portion of the human anatomy; body part) is needed.

The present example systems and methods may be applied, for example, to medical procedures that employ photon energy beams, particle beams, and/or high-intensity focused ultrasound. In such beam delivery based applications, the capacitive position sensing device may be made from materials that permit the passage of the beam with suitable transparency (e.g. greater than 80%, greater than 90%, greater than 95%, greater than 99%, or greater than 99.5% flux and/or intensity). In order to meet such constraints, the electrodes can be formed from a thin metallic layer, such as a thin layer of conductive paint or a thin metallic layer deposited on a substrate such as aluminized Mylar® or Kapton®. In one example implementation, the electrodes may be formed from a material having a conductive exceeding 32 ohms for a 10 mm×10 mm section. The electrodes may be connected via a conductor to capacitance detector (e.g. a circuit which measures capacitance). This conductor may be comprised of a shielded cable or shielded trace (e.g. formed from a thin metal layer or conductive paint), but it must not significantly attenuate the radiation therapy beam. In some example embodiments, adjacent capacitive pads in the array may be separated by dielectric (as in the present embodiment) or alternatively by additional conductive elements at a different potential from the capacitive pads, for example, at 0V (such as in the "parallel fingers" configuration). If the additional conductive elements are provided at a similar potential as the capacitive sensing electrodes, the electric field may be confined by the presence of the additional conductive elements.

The substrate 120 may consist of a material that is durable but also introduces minimal attenuation of the radiation beam, for example, a thin-walled, hollow or close-cell foam-filled carbon-fiber shell.

In other example embodiments, the capacitive positioning sensing device may include an aperture that permits the delivery of the beam to the body region.

Example applications of the embodiments disclosed above include stereotactic radiosurgery and radiotherapy (e.g. cranial surgery). It is to be understood, however, that the radiosurgical and radiotherapeutic applications are merely provided as example applications, and that the systems and methods described herein can be applied to many other applications, such as, but not limited to, navigated surgical procedures, robotic surgery and imaging procedures. The methods provided herein may additionally or alternatively be employed to pre-operatively screen patients for surgical interventions in order to determine whether or not a given patient is likely to be capable of maintaining a positional range during a time duration associated with a medical procedure.

Radiosurgery and Radiotherapy Applications

Example applications of the embodiments disclosed above include stereotactic radiosurgery and radiotherapy. Such applications may involving the following constraints: absence of highly-attenuating materials in the paths of the incoming radiation beams, which would perturb the treatment delivery; capacity to read-out the position of the patient at high temporal frequency (e.g., many times per second); measurement of patient position in two or three dimensions; the ability to monitor the position of the cranium as a whole, rather than, e.g., just the skin; and absence of unwanted ionizing radiation (e.g., unlike imaging using x-rays). The embodiments disclosed herein may be adapted to meet these requirements. For cranial indications, the device could introduce the options of i) eliminating the invasive head-ring, replacing with the head-ring with mask immobilization combined with real-time monitoring, or ii)

monitoring of the cranium for existing treatments that employ rigid mask immobilization. Given the use of extremely thin conductive elements, the device does not introduce significantly attenuating materials around the patient, meaning that the delivery of radiation is not perturbed. This would not be the case for other detection systems, e.g., pressure sensors or ultrasonic transducers.

Use of Capacitive Position Sensing Device with Mask

Figure 11:
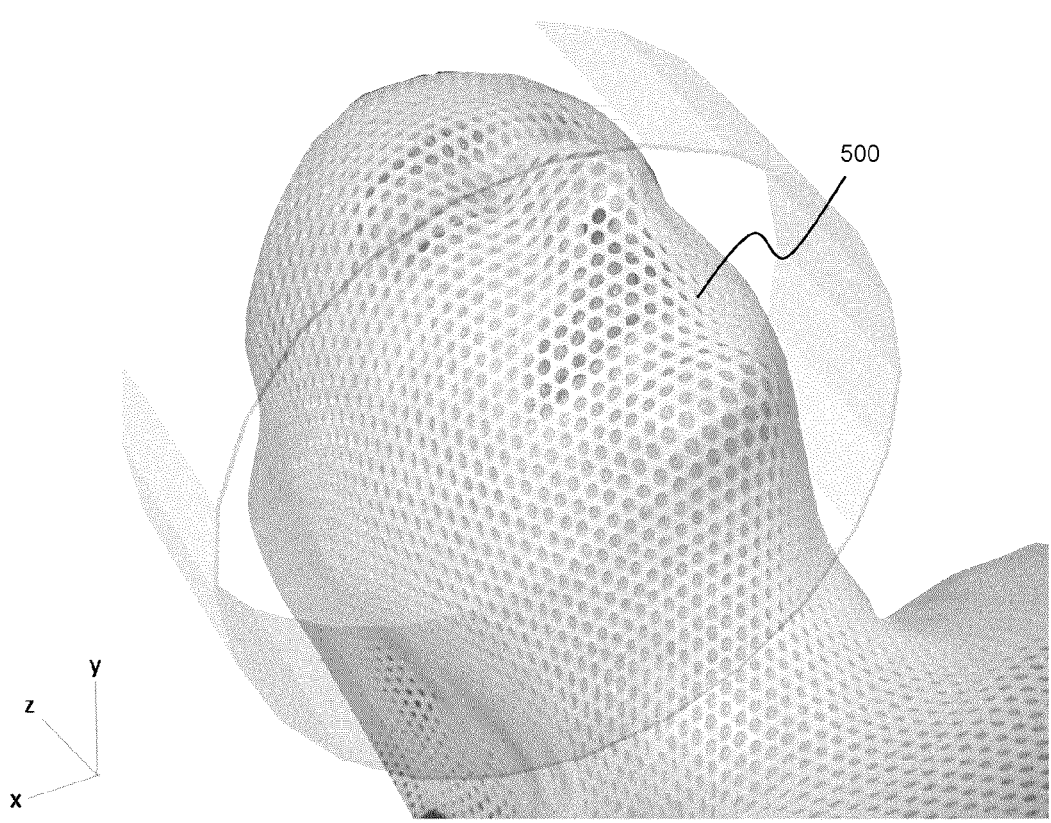
FIG. 11 illustrates an example implementation in which a cylindrical capacitive position sensing device is employed for measuring positional offsets of a patient's head, where a thermoplastic immobilization mask is positioned adjacent to the patient's head, and wherein the capacitance valves are measured through the thermoplastic immobilization mask.

In some embodiments, a mask, or other restraining or immobilization device having a dielectric structure, may be placed between the body region and the capacitive position sensing device. It will be understood that the phrase "mask", as used herein, refers to a restraining or immobilization structure that is placed adjacent to the region of the body. For example, the mask 500 may be a thermoplastic mask configured to restrain the head of the patient during a medical procedure, as illustrated in FIG. 11. If a patient is positioned within a such a thermoplastic mask, the capacitance position sensing device will not track the mask position (which is not of interest and may be a poor surrogate for patient position due to the motion of the patient relative to the mask), and instead tracks the position of the patient within the mask. Such a mask may be employed to define the reference position, such that the positional offsets are measured relative to the mask, thereby tracking patient motion relative to the mask. The mask may be employed during calibration measurements, or included in calibration simulations, in order to account for the presence and effect of the dielectric on the measured capacitance values.

Figure 12:
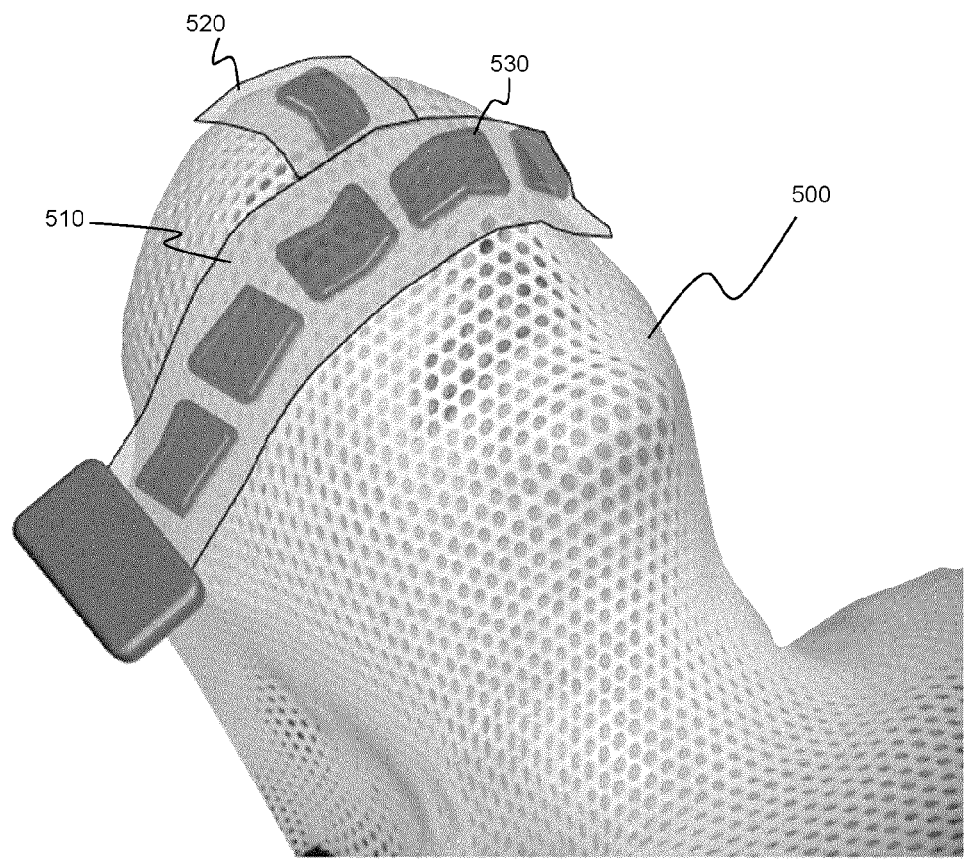
FIG. 12 illustrates an example embodiment in which capacitive electrode elements are coupled directly to, or immediately proximal to, the surface of the mask.

In one example embodiment, the mask may define the dielectric substrate of the capacitance position sensing device, or at least a portion thereof, such that the electrodes are provided on or within the mask. For example, the electrodes may be embedded within the mask or provided on the inner or outer surface of the mask. In one example embodiment, the electrodes may be formed on, or attached to, the outer surface of the mask, optionally via an additional supporting dielectric structure that contacts the mask. An example of the latter is shown in FIG. 12, where one or more flexible dielectric structures 510, 520 (e.g. tape) is employed to attach (mechanically couple) the capacitive sensing electrodes 530 directly to, or immediately proximal to, the surface of the mask 500. The use of such flexible structures (e.g. tape or flexible bands) could replicate any of the geometries shown in the previous figures in order to provide detection of motion in x, y and z dimensions. The flexible bands could be adhesive, or individually adjustable in order to conform to various mask shapes.

Figure 13:
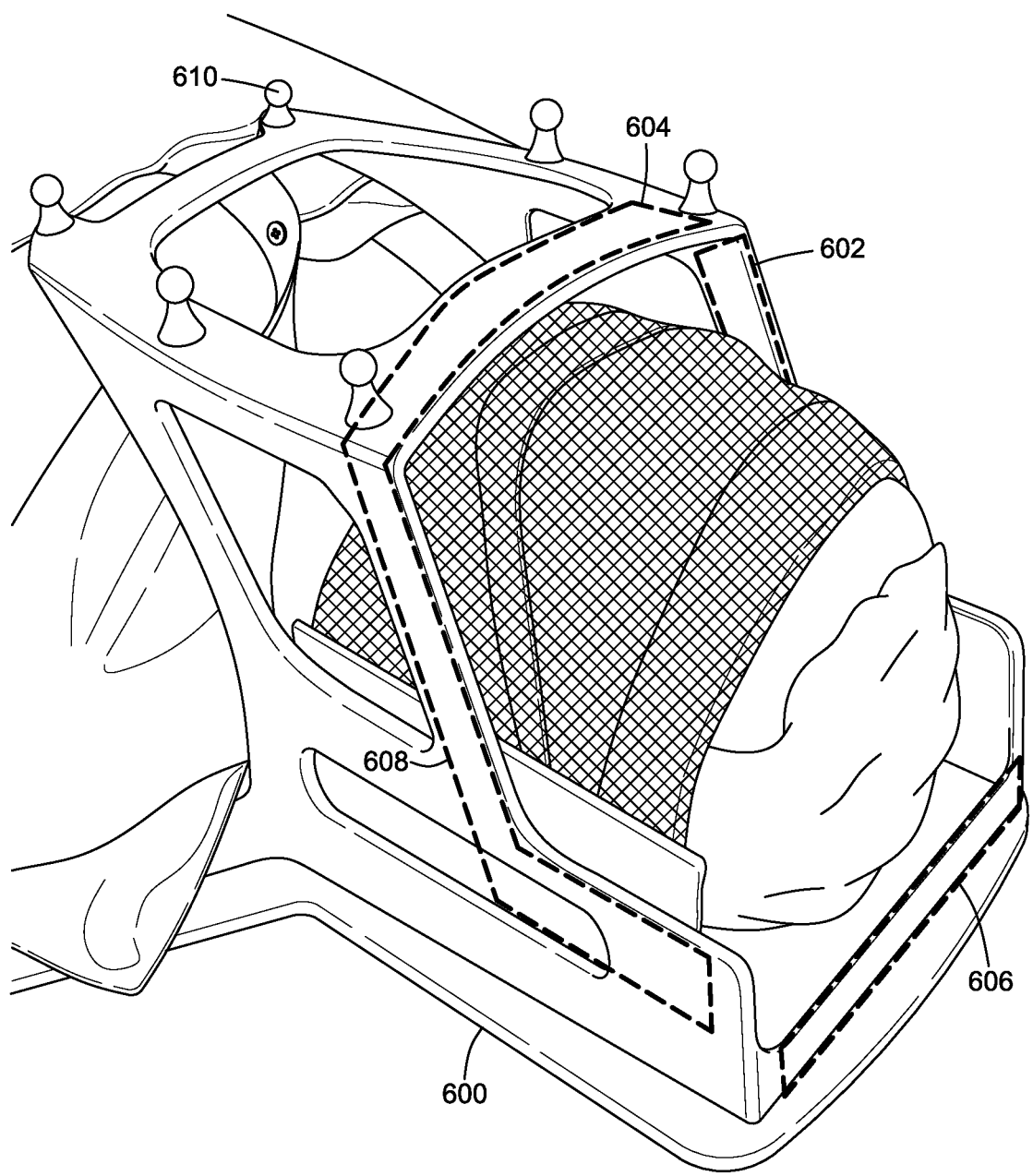
FIG. 13 is a photograph illustrating an example implementation in which a thermoplastic mask supported by an additional support structure, and where the capacitive position sensing device is integrated with the additional support structure.

Referring now to FIG. 13, some existing patient positioning systems involve additional structural support surrounding the thermoplastic mask. For example, the device shown in FIG. 13 employs a frameless support structure 600 made of low-density carbon fibre (a "frameless array"). Reflective fiducial markers 610 (spheres on anterior surface in image) are shown as being provided in order to track the position of the support structure 600, but these fiducials do not track the position of the cranium itself.

In one example embodiment, the support structure 600 (optionally without the fiducial markers 610) could be employed to support the array of electrodes of the capacitive position detection system. For example, suitable positions for the inclusion of capacitive position sensing electrodes on the support structure 600 are overlaid on the image shown in FIG. 13 in dashed lines (see labels 602, 604, 606 and 608). In one example implementation, the electrodes could be provided on thin dielectric support layers, which could be attached to, for example, the inner surface of the carbon fibre frame 600.

Capacitive Sensing of Angular Offset

In some embodiments, the capacitive position sensor device may be employed to detect changes in angular orientation in addition to, or in alternative to, the position sensing embodiments described above. For example, the calibration data set described above may be configured to include angular-dependent calibration data in addition to, on instead of, the positional data. In cases in which the calibration data includes both position and angular calibration data, both the positional and angular offset may be monitored, thereby providing for the monitoring of six degrees of freedom in selected embodiments.

Such embodiments may be useful to correct for misalignments in systems that are equipped with robotic compensation that can remove x, y, z as well as roll, pitch and yaw errors. Similar to the idea of shifting the array by known amounts and reading out capacitance values, the array could be rotated about the three axes by known amounts. It is noted that in some embodiments, the angular offset detection may be performed over a subset of the three angular axes. Alternatively, in some cases, small angular perturbation may be approximated by positional offsets. For example, the pitch motion is the most common in cranial patients (i.e. nodding) but the centre of rotation is quite inferior, so this translates into displacement in both the anterioposterior and superioinferior axes.

EXAMPLES

The following examples are presented to enable those skilled in the art to understand and to practice embodiments of the present disclosure. They should not be considered as a limitation on the scope of the disclosure, but merely as being illustrative and representative thereof.

Example Capacitive Position Sensing Device

The example capacitive position sensing device shown in FIG. 1A, consisting of a very low density ring with an array of conductive pads on the cylindrical inner surface, was fabricated as a prototype. The materials were selected to be minimally attenuating to MV therapeutic x-ray beams. In the example prototype, the dielectric support ring 120 was formed from 10% fill polylactic acid (PLA) produced by a 3D printer, however other materials would be possible in a commercial version, e.g., carbon fibre laminating a foam or hollow core. The conductive pads (shown black in the diagram) were formed from a very thin layer of a conductive paint (Bare Conductive, UK). The patient anatomy (e.g., head or other anatomy) would be located within the ring. As noted above, other non-ring geometries are possible, and the device could be made to adapt readily into existing mask immobilization systems commonly used in RT or SRS.

A computer was programmed to reads out the signals from all conductive pads (up to 12 at a time in the present example case), and calculate position of the anatomy inside the ring. The position was shown graphically on a display device.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention has a number of aspects. Non-limiting aspects of the invention include, without limitation:

1. A method of performing capacitive monitoring the position of a body region during a medical procedure involving a therapeutic or surgical device, the method comprising:

positioning the body region in a reference position associated with the medical procedure, wherein at least a portion of the body region is positioned within a sensing region of a capacitive position sensing device, the capacitive position sensing device comprising an array of electrodes, and wherein the body region is positioned without contacting the array of electrodes;

detecting capacitance between each electrode and the body region, thereby obtaining a set of measured capacitance values;

processing the set of measured capacitance values to determine a positional offset of the body region relative to the reference position; and controlling the therapeutic or surgical device based on the positional offset.

2. The method according to aspect 1 wherein the array of electrodes are arranged in a three-dimensional configuration, and wherein the positional offset of the body region is determined in three dimensions.

3. The method according to aspect 1 or 2 wherein the processing of the set of measured capacitance values comprises:

obtaining calibration data for each electrode of the array of electrodes, the calibration data establishing a relationship, for each electrode, between capacitance and positional offset;

processing the set of measured capacitance values and the calibration data to determine positional offsets that result in a set of calibration capacitance values for the array of electrodes that best matches the set of measured capacitance values.

4. The method according to aspect 3 wherein the calibration data is obtained from calibration measurements of the body region obtained at a plurality of known positions relative to the reference position.

5. The method according to aspect 4 wherein the calibration measurements are obtained prior to the medical procedure.

6. The method according to aspect 3 wherein the calibration data is obtained from calibration measurements of a body part of another subject obtained at a plurality of known positions relative to the reference position, wherein the calibration measurements are obtained prior to the medical procedure.

7. The method according to aspect 3 wherein the calibration data is obtained from calibration measurements of a phantom body part obtained at a plurality of known positions relative to the reference position, wherein the calibration measurements are obtained prior to the medical procedure.

8. The method according to aspect 3 wherein the calibration data is obtained from plurality of finite element simulations, each finite element simulation comprising a set of capacitance values calculated at a unique spatial offset.

9. The method according to aspect 8 wherein the finite element simulations are performed based on patient-specific model data.

10. The method according to aspect 9 wherein the model data is obtained from previously measured volumetric image data associated with the patient undergoing the medical procedure.

11. The method according to any one of aspects 1 to 10 wherein controlling the therapeutic or surgical device comprises providing a signal to interrupt the operation of the therapeutic or surgical device when the positional offset exceeds a threshold offset.

12. The method according to aspect 11 wherein the positional offset comprises a plurality of positional offsets, wherein each positional offset is associated with a different spatial direction or dimension.

13. The method according to aspect 12 wherein each positional offset has a separate threshold offset associated therewith, and wherein the signal is provided to the therapeutic or surgical device when one or more of the thresholds are exceeded.

14. The method according to any one of aspects 1 to 10 wherein controlling the therapeutic or surgical device comprises providing the positional offset to the therapeutic or surgical device such that the therapeutic or surgical device can compensate for changes in the position of the body region.

15. The method according to any one of aspects 1 to 10 wherein controlling the therapeutic or surgical device comprises controlling a position and/or orientation of the therapeutic or surgical device to compensate for changes in the position of the body region.

16. The method according to any one of aspects 1 to 10 wherein controlling the therapeutic or surgical device comprises providing the positional offset to the therapeutic or surgical device or to a planning or navigation system associated with the therapeutic or surgical device, such that the location of one or more target locations associated with the medical procedure are dynamically updated.

17. The method according to any one of aspects 1 to 16 wherein the capacitive position sensing device houses at least a portion of the body region.

18. The method according to any one of aspects 1 to 16 wherein the array of electrodes surrounds at least a portion of the body region.

19. The method according to any one of aspects 1 to 16 wherein the array of electrodes are arranged in a spherical configuration.

20. The method according to aspect 19 wherein the array of electrodes comprises a first cylindrical array and at least one additional cylindrical array, wherein a first axis associated with the first cylindrical array and an additional axis associated with each additional cylindrical array are directed in different directions.

21. The method according to any one of aspects 1 to 20 wherein the therapeutic or surgical device is a robotic surgical device.

22. The method according to any one of aspects 1 to 20 wherein the therapeutic or surgical device delivers an energy beam selected from the group consisting of photon energy beams, particle beams, and high-intensity focused ultrasound.

23. The method according to aspect 22 wherein at least a portion of the capacitive position sensing device is formed from a material having a thickness and composition suitable for transmitting at least a portion of the energy beam during the medical procedure.

24. The method according to aspect 23 wherein the portion of the capacitive position sensing device comprises electrodes formed from a thin film suitable for transmitting at least 95 percent of the energy beam.

25. The method according to aspect 22 wherein the capacitive position sensing device comprises an aperture configure to permit passage of the energy beam during the medical procedure, such that the energy beam is not occluded by the capacitive position sensing device.

26. The method according to any one of aspects 1 to 25 wherein the body region is supported in the absence of a stereotactic frame.

27. The method according to any one of aspects 1 to 26 wherein the body region is the head.

28. The method according to aspect 27 wherein the reference position is defined at least in part by a mask, and wherein the body region is placed adjacent to the mask, and wherein the mask is formed from a dielectric material such that at least some of the capacitance values are measured through the mask.

29. The method according to aspect 28 wherein one or both of the mask and a supporting structure associated therewith forms at least a portion of the capacitive position sensing device, such that the mask and/or the supporting structure comprises the array of electrodes, and wherein at least one dielectric layer is present between each electrode and the body region.

30. The method according to aspect 28 wherein the array of electrodes are adhered to an outer surface of one or both of the mask and a supporting structure associated therewith.

31. The method according to any one of aspects 28 to 30 wherein the mask is a patient-specific mask.

32. The method according to any one of aspects 1 to 31 wherein the
positional offset of the body region relative to the reference position is determined at a rate exceeding 1 Hz.

33. The method according to any one of aspects 1 to 31 wherein the
positional offset of the body region relative to the reference position is determined at a rate exceeding 10 Hz.

34. The method according to any one of aspects 1 to 33 further comprising processing the set of measured capacitance values to determine an angular offset of the body region about one or more axes relative to the reference position; and
controlling the therapeutic or surgical device based on both the positional offset and the angular offset.

35. A method of performing capacitive monitoring of the orientation of a body region during a medical procedure involving a therapeutic or surgical device, the method comprising:
positioning the body region in a reference orientation associated with the medical procedure, wherein at least a portion of the body region is positioned within a sensing region of a capacitive position sensing device, the capacitive position sensing device comprising an array of electrodes, and wherein the body region is positioned without contacting the array of electrodes;
detecting a capacitance between each electrode and the body region, thereby obtaining a set of measured capacitance values;
processing the set of measured capacitance values to determine a angular offset of the body region about one or more axes relative to the reference orientation; and
controlling the therapeutic or surgical device based on the angular offset.

36. A method of performing capacitive monitoring the position of a body region during a medical procedure, the method comprising:
positioning the body region in a reference position associated with the medical procedure, wherein at least a portion of the body region is positioned within a sensing region of a capacitive position sensing device, the capacitive position sensing device comprising an array of electrodes, and wherein the body region is positioned without contacting the array of electrodes;
detecting capacitance between each electrode and the body region, thereby obtaining a set of measured capacitance values;
processing the set of measured capacitance values to determine a positional offset of the body region relative to the reference position; and
providing an alert to interrupt the medical procedure when the positional offset exceeds a threshold.

37. A system for performing capacitive monitoring the position of a body region during a medical procedure involving a therapeutic or surgical device, the system comprising:
a capacitive position sensing device comprising:
a dielectric support; and
an array of electrodes provided on or embedded within said dielectric support;
wherein said array of electrodes is configured for capacitive sensing within a sensing region, wherein the sensing region is suitable for positioning at least a portion of the body region therein, such that the body region is positionable in a reference position within the sensing volume without contacting said array of electrodes;
control and processing hardware operatively coupled to said capacitive position sensing device, wherein said control and processing hardware is connectable to said therapeutic or surgical device for sending a control signal thereto, and wherein said control and processing hardware is configured to perform operations comprising:
detecting capacitance between each electrode and the body region, thereby obtaining a set of measured capacitance values;
processing the set of measured capacitance values to determine a positional offset of the body region relative to the reference position; and
providing the control signal to the therapeutic or surgical device based on the positional offset.

38. The system according to aspect 37 wherein said array of electrodes are arranged in a three-dimensional configuration, and wherein the positional offset of the body region is determined in three dimensions.

39. The system according to aspect 37 wherein the processing of the set of measured capacitance values comprises:
obtaining calibration data for each electrode of the array of electrodes, the calibration data establishing a relationship, for each electrode, between capacitance and positional offset;
processing the set of measured capacitance values and the calibration data
to determine positional offsets that result in a set of calibration capacitance values for said array of electrodes that best matches the set of measured capacitance values.

40. The system according to aspect 39 wherein the calibration data pertains to calibration measurements of the body region obtained at a plurality of known positions relative to the reference position.

41. The system according to aspect 39 wherein the calibration data is obtained from plurality of finite element simulations, each finite element simulation comprising a set of capacitance values calculated at a unique spatial offset.

42. The system according to any one of aspects 37 to 41 wherein controlling the therapeutic or surgical device comprises providing a signal to interrupt the operation of the therapeutic or surgical device when the positional offset exceeds a threshold offset.

43. The system according to aspect 42 wherein the positional offset comprises a plurality of positional offsets, wherein each positional offset is associated with a different spatial direction or dimension.

44. The system according to aspect 43 wherein each positional offset has a separate threshold offset associated therewith, and wherein the signal is provided to said therapeutic or surgical device when one or more of the thresholds are exceeded.

45. The system according to any one of aspects 37 to 41 wherein controlling said therapeutic or surgical device comprises providing the positional offset to said therapeutic or surgical device such that said therapeutic or surgical device can compensate for changes in the position of the body region.

46. The system according to any one of aspects 37 to 41 wherein controlling said therapeutic or surgical device comprises controlling a position and/or orientation of the therapeutic or surgical device to compensate for changes in the position of the body region.

47. The system according to any one of aspects 37 to 41 wherein controlling said therapeutic or surgical device comprises providing the positional offset to said therapeutic or surgical device or to a planning or navigation system associated with
the therapeutic or surgical device, such that the location of one or more target locations associated with the medical procedure are dynamically updated.

48. The system according to any one of aspects 37 to 47 wherein said array of electrodes are arranged in a spherical configuration.

49. The system according to aspect 48 wherein said array of electrodes comprises a first cylindrical array and at least one additional cylindrical array, wherein a first axis associated with said first cylindrical array and an additional axis associated with each additional cylindrical array are directed in different directions.

50. The system according to any one of aspects 37 to 49 wherein said dielectric support comprises an outer dielectric layer provided on said array of electrodes, and wherein an outer shielding layer is provided on said outer dielectric layer.

51. The system according to any one of aspects 37 to 49 wherein said dielectric support comprises an outer dielectric layer provided on said array of electrodes, and wherein a field focusing layer is provided on or within said outer dielectric layer.

52. The system according to any one of aspects 37 to 51 wherein said therapeutic or surgical device is a robotic surgical device.

53. The system according to any one of aspects 37 to 51 wherein said therapeutic or surgical device delivers an energy beam selected from the group consisting of photon energy beams, particle beams, and high-intensity focused ultrasound.

54. The system according to aspect 53 wherein at least a portion of said capacitive position sensing device is formed from a material having a thickness and composition suitable for transmitting at least a portion of the energy beam during the medical procedure.

55. The system according to aspect 54 wherein the portion of said capacitive position sensing device comprises electrodes formed from a thin film suitable for transmitting at least 95 percent of the energy beam.

56. The system according to aspect 53 wherein said capacitive position sensing device comprises an aperture configure to permit passage of the energy beam during
the medical procedure, such that the energy beam is not occluded by said capacitive position sensing device.

57. The system according to any one of aspects 37 to 56 further comprising a mask, wherein said mask is configured for positioning the body region adjacent thereto when the body part is positioned in the reference position, and wherein said mask is formed from a dielectric material such that at least some of the capacitance values are measured through said mask.

58. The system according to aspect 57 wherein one or both of said mask and a supporting structure associated therewith forms at least a portion of said capacitive position sensing device, such that said mask and/or said supporting structure comprises said array of electrodes, and wherein at least one dielectric layer is present between each electrode and the body region when the body region is placed adjacent to said mask.

59. The system according to aspect 57 wherein said array of electrodes are adhered to an outer surface of one or both of said mask and a supporting structure associated therewith.

60. The system according to any one of aspects 57 to 59 wherein said mask is a patient-specific mask.

61. The system according to any one of aspects 37 to 60 wherein said control and processing hardware is configured such that the positional offset of the body region relative to the reference position is determined at a rate exceeding 1 Hz.

62. The system according to any one of aspects 37 to 60 wherein said control and processing hardware is configured such that the positional offset of the body region relative to the reference position is determined at a rate exceeding 10 Hz.

63. The system according to any one of aspects 37 to 62 wherein said control and processing hardware is further configured to perform operations comprising:
processing the set of measured capacitance values to determine an angular offset of the body region about one or more axes relative to the reference position; and
controlling the therapeutic or surgical device based on both the positional offset and the angular offset.

64. A system for performing capacitive monitoring the position of a body region during a medical procedure, the system comprising:
a capacitive position sensing device comprising:
a dielectric support; and
an array of electrodes provided on or embedded within said dielectric support;
wherein said array of electrodes is configured for capacitive sensing within a sensing region, wherein the sensing region is suitable for positioning at least a portion of the body region therein, such that the body region is positionable in a reference position within the sensing volume without contacting said array of electrodes;
control and processing hardware operatively coupled to said capacitive position sensing device, wherein said control and processing hardware is configured to perform operations comprising:
detecting capacitance between each electrode and the body region, thereby obtaining a set of measured capacitance values;
processing the set of measured capacitance values to determine a positional offset of the body region relative to the reference position; and
providing an alert to interrupt the medical procedure when the positional offset exceeds a threshold.

What is claimed is:

1. A method of performing capacitive monitoring the position of a body region for a medical procedure involving a medical device, the method comprising:
    positioning the body region in a reference position within a sensing region of a capacitive position sensing device, the capacitive position sensing device comprising an array of electrodes;
    detecting capacitance between each electrode and the body region, thereby obtaining a set of measured capacitance values; and
    processing the set of measured capacitance values to determine an offset of the body region relative to the reference position;
    wherein the offset comprises a plurality of positional offsets, wherein each positional offset is associated with a different spatial direction or dimension.

2. The method according to claim 1, further including one or more of:
    controlling the medical device based on the offset; and
    providing an alert to interrupt the medical procedure when the offset exceeds a threshold.

3. The method according to claim 2 wherein controlling the medical device comprises providing a signal to interrupt the operation of the medical device when the offset exceeds a threshold offset.

4. The method according to claim 2 wherein controlling the medical device comprises providing the offset to the medical device such that the medical device can compensate for changes in the position of the body region.

5. The method according to claim 2 wherein controlling the medical device comprises controlling at least one of a position and an orientation of the medical device to compensate for changes in the position of the body region.

6. The method according to claim 2 wherein controlling the medical device comprises providing the offset to the medical device or to a planning or navigation system associated with the medical device, such that the location of one or more target locations associated with the medical procedure are dynamically updated.

7. The method according to claim 1, wherein the medical device is a therapeutic or surgical device.

8. The method according to claim 1 wherein the array of electrodes are arranged in a three-dimensional configuration, and wherein the offset is determined in three dimensions.

9. The method according to claim 1 wherein the processing of the set of measured capacitance values comprises:
    obtaining calibration data for each electrode of the array of electrodes, the calibration data establishing a relationship, for each electrode, between capacitance and offset;
    processing the set of measured capacitance values and the calibration data to determine offsets that result in a set of calibration capacitance values for the array of electrodes that best matches the set of measured capacitance values.

10. The method according to claim 9 wherein the calibration data is obtained from calibration measurements of the body region obtained at a plurality of known positions relative to the reference position.

11. The method according to claim 9 wherein the calibration data is obtained from a plurality of finite element simulations, each finite element simulation comprising a set of capacitance values calculated at a unique spatial offset.

12. The method according to claim 11 wherein the finite element simulations are performed based on patient-specific model data.

13. The method according to claim 12 wherein the model data is obtained from previously measured volumetric image data associated with the body region.

14. The method according to claim 1 wherein each positional offset has a separate threshold offset associated therewith, and wherein a control signal is provided to the medical device when one or more of the thresholds are exceeded.

15. The method according to claim 1 wherein the array of electrodes surrounds at least a portion of the body region when the body region is positioned in the sensing region.

16. The method according to claim 1 wherein the electrodes of the array of electrodes are arranged in a spherical configuration.

17. The method according to claim 1 wherein the array of electrodes comprises a first cylindrical array and at least one additional cylindrical array, wherein a first axis associated with the first cylindrical array and an additional axis associated with each additional cylindrical array are directed in different directions.

18. The method according to claim 1 wherein the medical device delivers an energy beam selected from the group consisting of photon energy beams, particle beams, and high-intensity focused ultrasound.

19. The method according to claim 1 wherein at least a portion of the capacitive position sensing device is formed from a material having a thickness and composition suitable for transmitting at least a portion of an energy beam during the medical procedure.

20. The method according to claim 19 wherein the portion of the capacitive position sensing device comprises electrodes formed from a thin film suitable for transmitting at least 95 percent of the energy beam.

21. The method according to claim 1 wherein the capacitive position sensing device comprises an aperture configured to permit passage of an energy beam during the medical procedure, such that the energy beam is not occluded by the capacitive position sensing device.

22. The method according to claim 1 wherein the reference position is defined at least in part by a mask, and wherein the body region is placed adjacent to the mask, and wherein the mask is formed from a dielectric material such that at least some of the capacitance values are measured through the mask.

23. The method according to claim 22 wherein one or both of the mask and a supporting structure associated therewith forms at least a portion of the capacitive position sensing device, such that the mask and/or the supporting structure comprises the array of electrodes, and wherein at least one dielectric layer is present between each electrode and the body region.

24. The method according to claim 1 further comprising processing the set of measured capacitance values to determine an angular offset of the body region about one or more axes relative to the reference position.

25. The method according to claim 24 further comprising controlling the medical device based on both the plurality of positional offsets and the angular offset.

26. The method according to claim 1, comprising providing a control signal to the medical device based on the offset, wherein the control signal is indicative of one or both of a positional offset and an angular offset.

27. A method of performing capacitive monitoring the position of a body region for a medical procedure involving a medical device, the method comprising:

positioning the body region in a reference position within a sensing region of a capacitive position sensing device, the capacitive position sensing device comprising an array of electrodes;

detecting capacitance between each electrode and the body region, thereby obtaining a set of measured capacitance values; and processing the set of measured capacitance values to determine an offset of the body region relative to the reference position;

wherein the offset comprises an angular offset.

28. A system for performing capacitive monitoring the position of a body region for a medical procedure involving a medical device, the system comprising:

a capacitive position sensing device comprising:

an array of electrodes configured for capacitive sensing within a sensing region, wherein the sensing region is suitable for positioning the body region in a reference position therein;

control and processing hardware operatively coupled to the capacitive position sensing device, wherein the control and processing hardware is configured to perform operations comprising:

detecting capacitance between each electrode and the body region, thereby obtaining a set of measured capacitance values;

processing the set of measured capacitance values to determine an offset of the body region relative to the reference position;

wherein the offset comprises a plurality of positional offsets, wherein each positional offset is associated with a different spatial direction or dimension.

29. A system for performing capacitive monitoring the position of a body region for a medical procedure involving a medical device, the system comprising:

a capacitive position sensing device comprising:

an array of electrodes configured for capacitive sensing within a sensing region, wherein the sensing region is suitable for positioning the body region in a reference position therein;

control and processing hardware operatively coupled to the capacitive position sensing device, wherein the control and processing hardware is configured to perform operations comprising:

detecting capacitance between each electrode and the body region, thereby obtaining a set of measured capacitance values;

processing the set of measured capacitance values to determine an offset of the body region relative to the reference position;

wherein the offset comprises an angular offset.

* * * * *